United States Patent
Cattolica et al.

(10) Patent No.: US 11,224,865 B2
(45) Date of Patent: Jan. 18, 2022

(54) CATALYST FOR THE METHANATION OF SYNGAS AND PRODUCER GAS

(71) Applicant: THE REGENTS OF THE UNIVERSITY OF CALIFORNIA, Oakland, CA (US)

(72) Inventors: Robert Cattolica, San Diego, CA (US); Reinhard Seiser, La Jolla, CA (US); Tinku Baidya, Hyderabad (IN)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/577,925

(22) Filed: Sep. 20, 2019

(65) Prior Publication Data
US 2020/0094227 A1    Mar. 26, 2020

Related U.S. Application Data

(60) Provisional application No. 62/736,318, filed on Sep. 25, 2018.

(51) Int. Cl.
| | |
|---|---|
| *B01J 23/89* | (2006.01) |
| *B01J 23/755* | (2006.01) |
| *B01J 23/78* | (2006.01) |
| *B01J 23/58* | (2006.01) |
| *B01J 21/04* | (2006.01) |
| *B01J 35/10* | (2006.01) |
| *B01J 37/02* | (2006.01) |
| *C07C 1/04* | (2006.01) |
| *B01J 23/46* | (2006.01) |

(52) U.S. Cl.
CPC .......... *B01J 23/8946* (2013.01); *B01J 21/04* (2013.01); *B01J 23/462* (2013.01); *B01J 23/58* (2013.01); *B01J 23/755* (2013.01); *B01J 23/78* (2013.01); *B01J 35/1009* (2013.01); *B01J 35/1014* (2013.01); *B01J 35/1019* (2013.01); *B01J 37/0201* (2013.01); *C07C 1/0435* (2013.01); *C07C 1/04* (2013.01); *C07C 2521/04* (2013.01); *C07C 2523/02* (2013.01); *C07C 2523/46* (2013.01); *C07C 2523/755* (2013.01); *C07C 2523/89* (2013.01)

(58) Field of Classification Search
None
See application file for complete search history.

(56) References Cited

U.S. PATENT DOCUMENTS 3,988,334 A * 10/1976 Finch ............... B01J 23/85
518/714

OTHER PUBLICATIONS

Mierczynski, P. et al. Carbon Deposits Formed on the Surface of Ru—Ni Catalysts During the Mixed Reforming of Methane Process Kinetics and Catalysis vol. 59, pp. 372-377(2018), Published Jun. 6, 2018 (Year: 2018).*
Analytical document (Published Sep. 5, 2016, pp. 1-3) (Year: 2016).*
Gao, Z. et al. "Selective methanation of CO over Ni/Al2O3 catalyst: Effects of preparation method and Ru addition" International Journal of Hydrogen Energy 41 (2016), 5484-5493 (Year: 2016).*
Hu, D. et al. "Enhanced Investigation of CO Methanation over Ni/Al2O3 Catalysts for Synthetic Natural Gas Production" Ind. Eng. Chem. Res. 2012, 51, 4875-4886 (Year: 2012).*
Lv, Y. et al. "Effect of La, Mg and Mo additives on dispersion and thermostability of Ni species on KIT-6 for CO methanation" Applied Catalysis A, General 543 (2017) 125-132 (Year: 2017).*
Liu, Y. et al. "Homogeneous and highly dispersed Ni—Ru on a silica support as an effective CO methanation catalyst" RSC Adv. 2018, 8, 2123, Published Jan. 8, 2018 (Year: 2018).*
Mirodatos, C. et al. Deactivation of Nickel based Catalysts during CO Methanation and Disproportionation. J.Catal. 1987, 107 (2), 275-287 (Year: 1987).*
Arakawa et al., Catalysis research of relevance to carbon management: progress, challenges, and opportunities, Chem Rev, 2001, pp. 953-996, vol. 101.
Aziz et al., Highly Active Ni-Promoted Mesostructured Silica Nanoparticles for CO2 Methanation, Appl Catal B: Environ, 2014, pp. 359-368, vol. 147.
Bligaard et al., The Brønsted-Evans-Polanyi relation and the volcano curve in heterogeneous catalysis, J. Catal., 2004, pp. 206-217, vol. 224.
Borgschulte et al., Sorption enhanced CO2 methanation, Phys Chem Chem Phys, 2013, pp. 9620-9625, vol. 15.
Dagle et al., Selective CO methanation catalysts for fuel processing applications, Appl Catal A: Gen, 2007, pp. 213-218, vol. 326.
Eckle et al., Activity, selectivity, and adsorbed reaction intermediates/ reaction side products in the selective methanation of CO in reformate gases on supported Ru catalysts, J. Catal, 2010, pp. 255-268, vol. 269.
Fan et al., Mg—Al oxide supported Ni catalysts with enhanced stability for efficient synthetic natural gas from syngas, Appl Surf Sci, 2014, pp. 682-688, vol. 307.
Gao et al., Recent advances in methanation catalysts for the production of synthetic natural gas, RSC Adv, 2015, p. 22759-22776, vol. 5.
Gierlich et al., Deactivation Phenomena of a Ni-based Catalyst for High Temperature Methanation, Elsevier, 1980, pp. 459-469.
Guo et al., The effect of impregnation strategy on structural characters and CO2 methanation properties over MgO modified Ni/SiO2 catalysts, Catal Commun, 2014, pp. 55-60, vol. 54.

(Continued)

*Primary Examiner* — Medhanit W Bahta
(74) *Attorney, Agent, or Firm* — Mintz, Levin, Cohn, Ferris, Glovsky and Popeo, P.C.

(57) ABSTRACT

Disclosed herein, inter alia, are novel nickel-ruthenium-magnesium oxide catalyst compositions and methods of making and using the same. The catalysts provide for improved methanation activity of syngas ($CO+H_2$) and producer gas in, for example, a fixed-bed reactor. In this manner, the CO conversion and $CH_4$ yield can be maximized in methanation reactions.

3 Claims, 22 Drawing Sheets
(19 of 22 Drawing Sheet(s) Filed in Color)

(56) References Cited

OTHER PUBLICATIONS

Gupta et al., Gas-Uptake, Methanation, and Microcalorimetric Measurements on the Coadsorption of CO and H2 over Polycrystalline Ru and a Ru/TiO2 Catalyst, J. Catal, 1997, pp. 423-437, vol. 169.

Janke et al., Catalytic and adsorption studies for the hydrogenation of CO2 to methane, Appl Catal B: Environ, 2014, pp. 184-191, vol. 152.

Kiendl et al., Dilute gas methanation of synthesis gas from biomass gasification, Fuel, 2014, pp. 211-217, vol. 123.

Kim et al., Bifunctional Mechanism of CO2 Methanation on Pd—MgO/SiO2 Catalyst: Independent Roles of MgO and Pd on CO2 Methanation, J. Phys Chem C, 2010, pp. 7128-7131, vol. 114.

Kondratenko et al., Status and perspectives of CO2 conversion into fuels and chemicals by catalytic, photocatalytic and electrocatalytic processes, J. Energy Environ Sci, 2013, pp. 3112-3135, vol. 6.

König et al., Methane synthesis and sulfur removal over a Ru catalyst probed in situ with high sensitivity X-ray absorption spectroscopy, J. Catal, 2013, pp. 92-100, vol. 305.

Konishcheva et al., Selective CO methanation in H2-rich stream over Ni-, Co- and Fe/CeO2: Effect of metal and precursor nature, Int J Hydrogen Energy, 2015, p. 14058-14063, vol. 40.

Kowalczyk et al., Supported ruthenium catalysts for selective methanation of carbon oxides at very low COx/H2 ratios, Appl Catal A: Gen, 2008, pp. 35-39, vol. 342.

Le et al., CO and CO2 methanation over supported Ni catalysts, Catalysis Today, 2017, pp. 89-96, vol. 293-294.

Lee et al., Raney Ni catalysts derived from different alloy precursors Part II. CO and CO2 methanation activity, Korean J Chem Eng, 2005, pp. 541-546, vol. 22.

Liu et al., Effect of CeO2 addition on Ni/Al2O3 catalysts for methanation of carbon dioxide with hydrogen, J. Nat Gas Chem, 2012, pp. 703-707, vol. 21.

Liu et al., Highly active and stable Ni/γ-Al2O3 catalysts selectively deposited with CeO2 for CO methanation, RSC Adv, 2014, p. 16094-16103, vol. 4.

Liu et al., Intercorrelation of structure and performance of Ni—Mg/Al2O3 catalysts prepared with different methods for syngas methanation, Catal Sci Technol, 2014, pp. 472-481, vol. 4.

Ma et al., Methanation of syngas over coral reef-like Ni/Al2O3 catalysts, J. Nat. Gas Chem., 2011, pp. 435-440, vol. 20.

Masini et al., Methanation on mass-selected Ru nanoparticles on a planar SiO2 model support: The importance of under-coordinated sites, J. Catal, 2013, pp. 282-290, vol. 308.

Nematollahi et al., Preparation of highly active and stable NiO—CeO2 nanocatalysts for CO selective methanation, Int J Hydrogen Energy, 2015, pp. 8539-8547, vol. 40.

Nematollahi et al., Selective methanation of carbon monoxide in hydrogen rich stream over Ni/CeO2 nanocatalysts, J. Rare Earth, 2015, pp. 619-628, vol. 33.

Ocampo et al., Effect of Ce/Zr composition and noble metal promotion on nickel based CexZr1—xO2 catalysts for carbon dioxide methanation, Appl Catal A: Gen, 2011, pp. 36-44, vol. 392.

Panagiotopoulou et al., Selective methanation of CO over supported noble metal catalysts: Effects of the nature of the metallic phase on catalytic performance, Appl Catal A: Gen, 2008, pp. 45-54, vol. 344.

Riani et al., Unsupported versus alumina-supported Ni nanoparticles as catalysts for steam/ethanol conversion and CO2 methanation, J. Mol Catal A: Chem, 2014, pp. 10-16, vol. 383-384.

Rombi et al., CO methanation on Ni—Ce mixed oxides prepared by hard template method, Appl Catal A: Gen, 2016, pp. 144-153, vol. 515.

Rnsch et al., Review on methanation—From fundamentals to current projects, Fuel, 2016, pp. 276-296, vol. 166.

Rotgerink et al., Studies on the promotion of nickel—alumina coprecipitated catalysts: II. Lanthanum oxide, Appl Catal, 1988, pp. 257-280, vol. 45.

Rotgerink et al., Studies on the promotion of nickel—alumina coprecipitated catalysts: III. Cerium oxide, Appl Catal, 1988, pp. 281-290, vol. 45.

Ryi et al., Production of synthetic natural gas by means of a catalytic nickel membrane, Fuel, 2012, pp. 64-69, vol. 94.

Sehested et al., Four challenges for nickel steam-reforming catalysts, Catal Today, 2006, pp. 103-110, vol. 111.

Sharma et al., CO2 methanation on Ru-doped ceria, J. Catal, 2011, pp. 297-309, vol. 278.

Song et al., Global challenges and strategies for control, conversion and utilization of CO2 for sustainable development involving energy, catalysis, adsorption and chemical processing, Catal Today, 2006, pp. 2-32, vol. 115.

Tada et al., Effect of metal addition to Ru/TiO2 catalyst on selective CO methanation, Catal Today, 2014, pp. 16-21, vol. 232.

Tada et al., Effect of Ru and Ni ratio on selective CO methanation over Ru—Ni/TiO2, Fuel, 2014, pp. 219-224, vol. 129.

Tada et al., Long-term durability of Ni/TiO2 and Ru—Ni/TiO2 catalysts for selective CO methanation, J. Power Sources, 2014, pp. 59-66, vol. 264.

Tada et al., Ni/CeO2 catalysts with high CO2 methanation activity and high CH4 selectivity at low temperatures, Int J Hydrogen Energy, 2012, pp. 5527-5531, vol. 37, No. 7.

Tada et al., Study of RuNi/TiO2 catalysts for selective CO methanation, Appl Catal B: Environ, 2013, pp. 258-264, vol. 140-141.

Takenaka et al., Complete removal of carbon monoxide in hydrogen-rich gas stream through methanation over supported metal catalysts, Int J Hydrogen Energy, 2004, pp. 1065-1073, vol. 29.

Thauer et al., Methanogenic archaea: ecologically relevant differences in energy conservation, Nat Rev Micro, 2008, pp. 579-591, vol. 6.

Vannice et al., The catalytic synthesis of hydrocarbons from $H_2$ + CO mixtures over the group VIII metals: II. The kinetics of the methanation reaction over supported metals, J. Catal., 1975, pp. 462-473, vol. 37.

Yao et al., Effect of cation-oligomer interactions on the size and reducibility of NiO particles on NiRu/SiO2 catalysts, J. Mater Chem, 2011, p. 17403-17412, vol. 21.

Yu et al., Synthetic natural gas from CO hydrogenation over silicon carbide supported nickel catalysts, Fuel Process Technol, 2011, pp. 2293-2298, vol. 92, No. 12.

Zhang et al., Carbon Nanofiber Supported Ni Catalysts for CO Methanation, Sci Adv Mater, 2011, pp. 1046-1051, vol. 3(6).

Zhang et al., Mixed-metal Pt monolayer electrocatalysis for oxygen reduction kinetics, J. Am Chem Soc, 2005, p. 12480-12481, vol. 127.

Zhao, et al., La promoted Ni/α—$Al_2O_3$ Catalysts for Syngas Methanation, World Academy of Science, Engineering and Technology, 2011, pp. 1002-1006, vol. 59.

Zhen, et al., Enhancing catalytic activity and stability for CO 2 methanation on Ni@MOF-5 via control of active species dispersion, Chemical Communications, 2014, p. 1728-1731, vol. 21.

Zhen, et al., Enhancing catalytic activity and stability for $CO_2$ methanation on Ni—Ru/Y—$Al_2O_3$ via modulating impregnation sequence and controlling surface active species, RSC Adv., 2014, p. 16472-16479, vol. 4.

\* cited by examiner

FIG. 16B
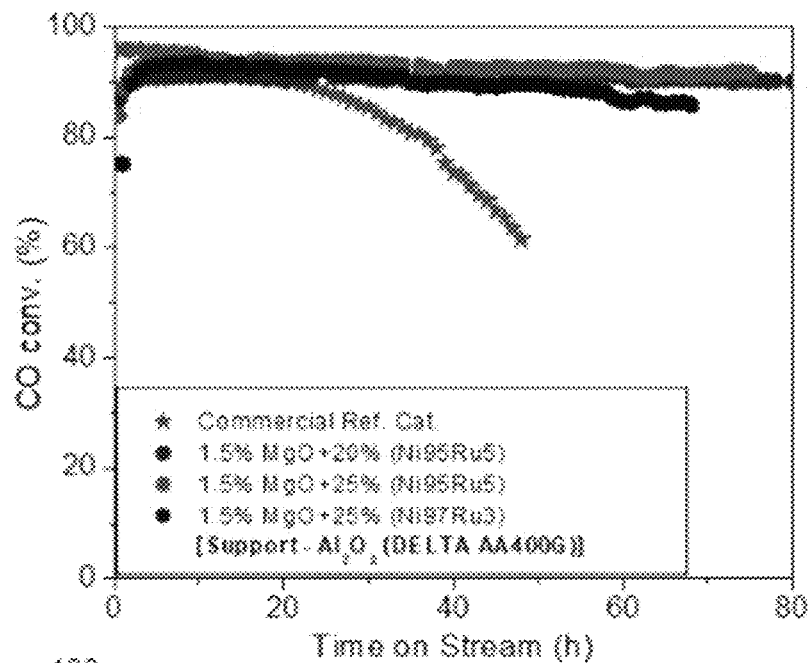
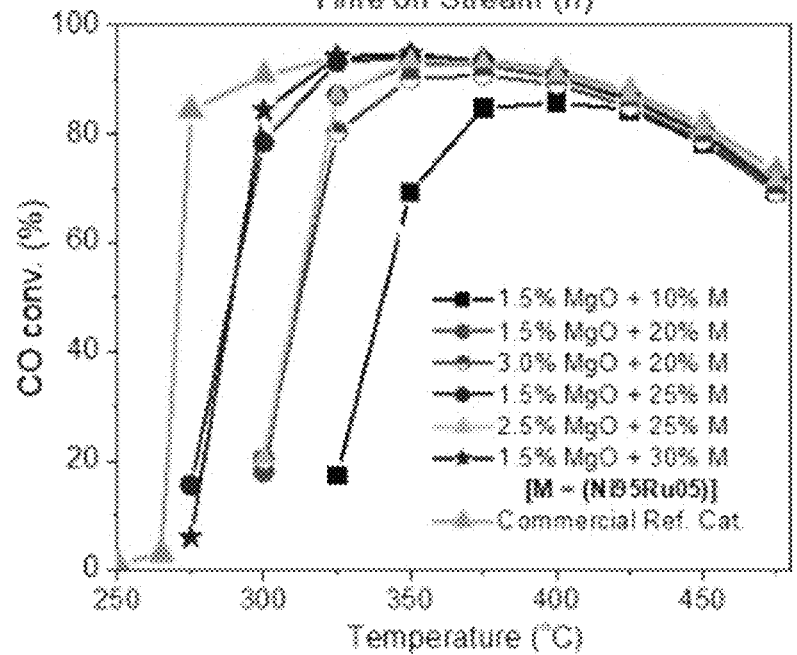
FIG. 16A

FIG. 20A
FIG. 20B
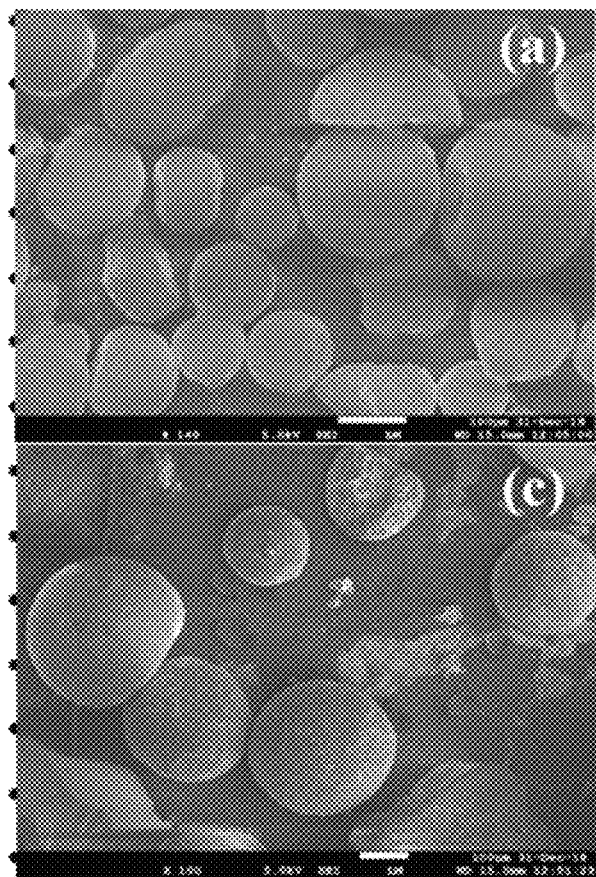
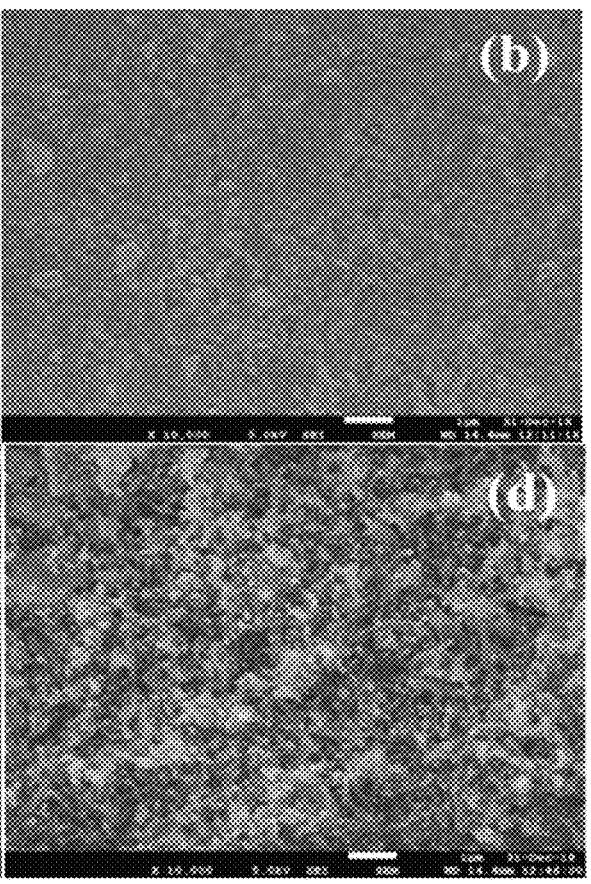
FIG. 20C
FIG. 20D

FIG. 21A
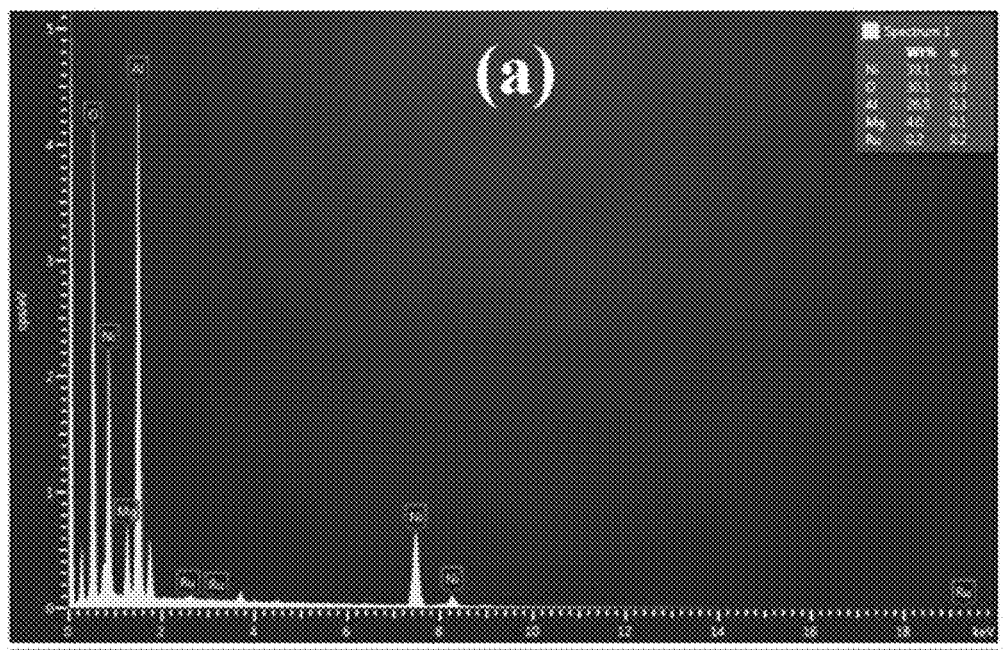
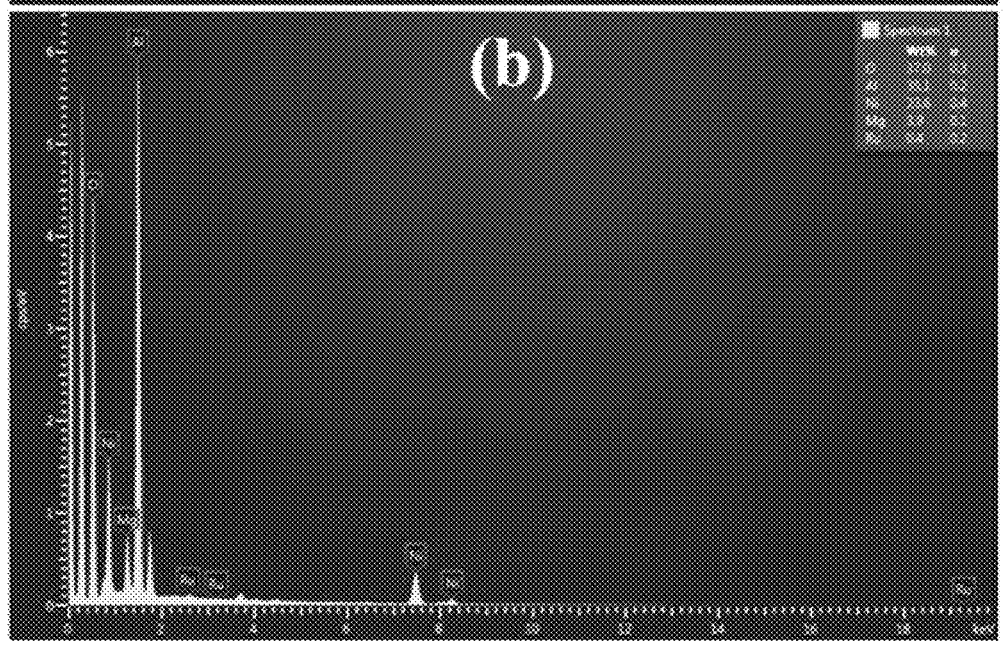
FIG. 21B

CATALYST FOR THE METHANATION OF SYNGAS AND PRODUCER GAS

CROSS REFERENCES TO RELATED APPLICATIONS

This application claims priority to U.S. Provisional Application No. 62/736,318 filed Sep. 25, 2018, the content of which is incorporated herein by reference in its entirety and for all purposes.

BACKGROUND

Natural gas consisting primarily of methane is an energy carrier with significant importance to the industry, and electricity, heating, and transportation sectors worldwide. The major source of methane comes from fossil natural gas resources. In recent years, interest in reducing the effect of fossil fuels on climate change has stimulated research on catalytic and biological production of methane from carbon oxide-rich gases (methanation). Biological methanation proceeds at low temperatures (<70° C.) in stirred tank reactors (Thauer R K, et al., *Nat Rev Micro* 2008; 6:579-91). Catalytic methanation occurs at temperatures above 250° C., mainly in fixed-bed reactors (Ronsch. S, et al., *Fuel* 2016: 166:276-96; Ma S, et al., *J. Nat. Gas Chem.,* 2011:20:435-40). Due to interest in the conversion of biomass into fuels, to reduce the carbon intensity of fuels, production of synthetic natural gas (SNG) from renewable biomass sources has attracted increased attention (Kiendl I, et al., *Fuel* 2014:123:211-17).

The key reactions for the SNG production process are: $CO+3H_2 \rightarrow CH_4+H_2O$, $\Delta H_{298K}=-206.1$ kJ/mol and $CO_2+4H_2 \rightarrow CH_4+2H_2O$, $\Delta H_{298K}=-164$ kJ/mol. These reactions can be used for methane production from a range of sources. Hydrogen production by photocatalytic or electrocatalytic water splitting powered by renewable energy (e.g., solar or wind) is regarded as future source of hydrogen for carbon dioxide hydrogenation. SNG production via the carbon dioxide methanation process can not only produce fuels and chemicals, but can also significantly reduce carbon dioxide emission to the atmosphere (Arakawa H, et al., *Chem Rev* 2001:101:953-96; Song C., *Catal Today* 2006:115:2-32; Kondratenko E V, et al., *Energy Environ Sci,* 2013:6:3112-35).

The catalytic methanation of $CO_x$ oxides is thermodynamically favorable at moderately to low temperatures, but due to the slow kinetics, catalysts play a very important role in the process. Many metals, such as Ni, Ru, Rh, Co, Fe, etc., have been used as methanation catalysts (Vannice M A, *J. Catal.,* 1975:37:462-73; Bligaard T, et al., *J Catal* 2004: 224:206-17; Gao J, et al., *RSC Adv* 2015:5:22759-76; Ronsch S, et al., *Fuel* 2016:166:276-96). However, some active metals including Ru and Rh are not economical for large-scale production of SNG due to their high cost. Ni is often regarded as the most practical choice because of its relatively high methanation activity and low cost (Ryi S K, et al., *Fuel* 2012:94:64-69; Riani P, et al., *J Mol Catal A: Chem* 2014:383-384:10-16; Lee G, et al., *Korean J Chem Eng* 2005:22:541-46). However, Ni catalysts can rapidly deactivate at high temperatures due to the sintering of Ni particles, facile carbon deposition, and severe sulfur poisoning (Sehested J., *Catal Today* 2006:111:103-10; Gierlich H H, et al., *Elsevier* 1980:459-69). The catalytic activity of Ni metal is dependent on the nature of the support oxides, stabilization of the Ni crystallites, and creation of adsorption sites for the reactants. Various supported Ni catalysts including $Al_2O_3$ (Ma S, et al., *J Nat Gas Chem* 2011:20:435-40; Takenaka S, et al., *Int J Hydrogen Energy* 2004:29:1065-73; Le T A, et al., *Catalysis Today* 2017:293-294:89-96), $SiO_2$ (Takenaka S., supra; Le T A., supra); MCM-41 (Aziz M A A, et al., *Appl Catal B: Environ* 2014:147:359-68), mesostructured silica nanoparticles (MSN) (Aziz M A A, supra), SiC (Yu Y, et al., *Fuel Process Technol* 2011:92(12):2293-98), HY (Aziz M A A, supra), 5A zeolite (Borgschulte A, et al., *Phys Chem Chem Phys* 2013:15:9620-25), $TiO_2$ (Le T A, supra), $ZrO_2$ (Le T A, supra), $CeO_2$ (Le T A, supra; Tada S, et al., *Int J Hydrogen Energy* 2012:37(7):5527-31; Nematollahi B, et al., *Int J Hydrogen Energy* 2015:40:8539-47; Konishcheva M V, et al., *Int J Hydrogen Energy* 2015:40: 14058-63; Nematollahi B, et al., *J. Rare Earth,* 2015, 33, 619-28; Rombi E, et al., *Appl Catal A: Gen* 2016:515:144-53); ceria-zirconia binary oxide (Ocampo F, et al., *Appl Catal A: Gen* 2011:392:36-44); metal-organic frameworks (MOFs) (Zhen W, et al., *Chem Commun* 2015:51:1728-31); and carbon nanofiber (CNF) (Zhang W, et al., *Sci Adv Mater* 2011:3(6):1046-51) have been studied for $CO_x$ methanation. Takenaka et al. (supra) compared the catalytic activity for CO methanation over supported Ni catalysts and concluded that $ZrO_2$ was the best support among $\gamma$-$Al_2O_3$, $SiO_2$, $TiO_2$, and $ZrO_2$.

Several effective promoters such as MgO (Guo M, et al., *Catal Commun* 2014:54:55-60; Fan M T, et al., *Appl Surf Sci* 2014:307:682-88; Kim H Y, et al., *J Phys Chem C* 2010: 114:7128-31), $La_2O_3$ (Rotgerink H G J L, et al., *Appl Catal* 1988:45:257-80; Zhao, A., et al., *Proc. World Acad. Sci. Eng. Tech.,* 2011, 59, 1002-1006; Tada S, et al., *Catal Today* 2014:232:16-21); $CeO_2$ (Liu H, et al., *J Nat Gas Chem* 2012:21:703-7; Rotgerink H G J L et al., *Appl Catal* 1988:45:281-90; Liu Q, et al., *RSC Adv* 2014:4:16094-103) have been used to enhance dispersion and thermal stability of Ni. The promoter's function has been related to better adsorption of $CO_x$ and thus help activation in the hydrogenation process. Among the promoters, MgO is very effective, inexpensive, and therefore widely used. It is known that NiO strongly interacts with MgO forming a solid solution that helps in formation of smaller Ni-metal particles during pretreatment with $H_2$.

Ruthenium is considered as the most active catalyst for methanation (Gupta N M, et al., *J Catal* 1997:169:423-37; J. Zhang, et al., *J Am Chem Soc* 2005:127:12480-81; Dagle A R, et al., *Appl Catal A: Gen* 2007:326:213-18; Panagiotopoulou P, et al., *Appl Catal A: Gen* 2008:344:45-54; Kowalczyk Z, et al., *Appl Catal A: Gen* 2008:342:35-39; Eckle S, et al., *J Catal* 2010:269:255-68; Sharma S, et al., *J Catal* 2011:278:297-309; Konig C F J, et al., *J Catal* 2013:305:92-100; Masini F, et al., *J Catal* 2013:308:282-90; Janke C, et al., *Appl Catal B: Environ* 2014:152:184-91). However, higher cost limits its industrial-scale application in SNG production. Ru also prevents carbon sintering and deposition, which makes the catalysts more resistant to deactivation (Konig C F J, supra). Therefore, the addition of Ru into Ni-forming Ni—Ru bimetallic catalysts has attracted extensive attention showing improved activity and stability of the catalysts (Zhen W, et al., *RSC Adv* 2014:4: 16472-79; Yao N, et al., *J Mater Chem* 2011:21:17403-12; Tada S, et al., *Fuel* 2014:129:219-24; Tada S, et al., *Appl Catal B: Environ* 2013:140-141:258-64; Tada S, et al., *J Power Sources* 2014:264:59-66; Tada S, et al., *Catal Today* 2014:232:16-21). The presence of Ru also enhanced the sulfur tolerance in the Ni-based catalyst. It is highly possible that Ni—Ru bimetallic combination in the presence of MgO could be a promising catalyst with the potential for improved methanation activity and stability.

There is a continued need for an effective method of producing syngas and the optimization of the combined promoting effects of the catalysts on the methanation activity.

BRIEF SUMMARY

In an aspect, provided herein is a catalyst including nickel (Ni), magnesium oxide (MgO), and ruthenium (Ru). In embodiments, the catalyst includes about 10 to 95 wt % Ni. In embodiments, the catalyst includes about 0.5 to 5.0 wt % MgO. In embodiments, the catalyst includes about 0.5 to 5 wt % Ru. In an aspect, the nickel-magnesium oxide-ruthenium catalyst, (e.g., a catalyst as described herein) demonstrates better performance at lower temperature with higher BET surface area support and higher catalyst loading.

In an aspect, provided herein is a method of making a nickel-magnesium oxide-ruthenium catalyst, (e.g., a catalyst as described herein), wherein the method includes (a) mixing nickel nitrate, magnesium nitrate, ruthenium chloride in a solvent; (b) combining the solution of step (a) with a substrate support to form a mixture; and maintaining the mixture of step (b) at a constant temperature for at least 12 hours. In embodiments, the method is described herein, e.g., in Examples 1 to 3.

In an aspect, provided herein is a method of making a nickel-magnesium oxide-ruthenium catalyst, (e.g., a catalyst as described herein) on a low BET surface area support, wherein the method includes (a) mixing nickel nitrate, magnesium nitrate, ruthenium chloride in a solvent; (b) combining the solution of step (a) with a substrate support to form a mixture; and maintaining the mixture of step (b) at a constant temperature for at least 12 hours. In embodiments, the method is described herein, e.g., in Examples 1 to 3.

In an aspect, provided herein is a method of making a nickel-magnesium oxide-ruthenium catalyst, (e.g., a catalyst as described herein) on a high BET surface area support, wherein the method includes (a) mixing nickel nitrate, magnesium nitrate, ruthenium chloride in a solvent; (b) combining the solution of step (a) with a substrate support to form a mixture; and maintaining the mixture of step (b) at a constant temperature for at least 12 hours. In embodiments, the method is described herein, e.g., in Example 4.

In an aspect, provided herein is a method of converting gas mixture to methane, said method comprising contacting the catalyst (e.g., a catalyst as described herein, including embodiments) with the gas mixture, wherein said gas mixture includes CO, $CO_2$, and $H_2$. In embodiments, the gas mixture further includes water.

BRIEF DESCRIPTION OF THE DRAWINGS

The patent or application file contains at least one drawings executed in color. Copies of this patent or patent application publication with color drawings will be provided by the Office upon request and payment of the necessary fee.

FIGS. 16A-16B. FIG. 16A: A comparison of methanation activity between Commercial reference catalyst and Mg—NiRu05 catalyst over DELTA AA400G alumina support with increasing loading of (Ni95Ru05) keeping MgO constant; FIG. 16B: Time-on-Stream in Methanation activity with producer gas mixture over commercial reference catalyst (at 350° C.), 1.5% Mg+20% (Ni95Ru05) (at 390° C.), 1.5% Mg+25% (Ni95Ru05) (at 350° C.) and 1.5% Mg+25% (Ni97Ru3) (at 350° C.) catalyst loaded over DELTA AA400G alumina support catalysts; GHSV=96,000 cc $min^{-1}$ $g_{cat}^{-1}$.

FIGS. 20A-20D. SEM images of Mg—NiRu05 catalyst for fresh (FIGS. 20A and 20B) and used (FIGS. 20C and 20D) conditions at low (×100) (A,C) and high (×10000) (B,D) magnifications.

FIGS. 21A and 21B. Elemental analysis of Mg—NiRu05 catalyst with EDX for fresh (FIG. 21A) and used (FIG. 21B) condition.

DETAILED DESCRIPTION

I. Definitions

Figure 1:
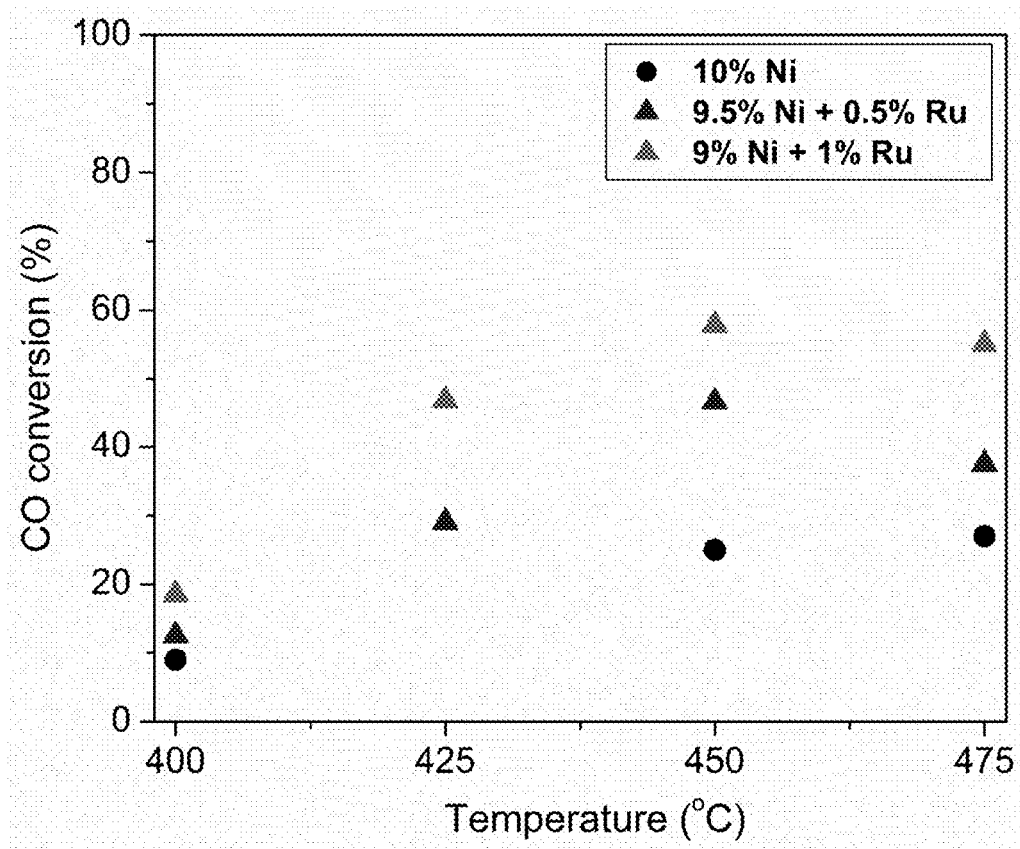
FIG. 1. Conversion of CO in producer gas over Ni catalyst with variation in Ru loading; GHSV—96000 cc $g_{cat}^{-1}$ $h^{-1}$.

The term "exemplary" is used to mean serving as an example, instance, or illustration. Any embodiment or design described herein as "exemplary" is not necessarily to be construed as preferred or advantageous over other embodiments or systems. Rather, use of the word exemplary is intended to present concepts in a concrete manner.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about means the specified value.

As defined herein, the term "reducing" and the like in reference to a method of reducing tar from a gas mixture means negatively affecting (e.g. decreasing) the level of tar of the gas mixture relative to the level of tar in the absence of the method. The term "reducing" also means removing oxygen from the oxidized catalyst.

The term "honeycomb" and "honeycomb structure" refers to a substrate support comprising a plurality of interconnected cell walls that define a plurality of cells (e.g., a lattice of cells). Typically many honeycomb core materials define hexagonal cells, the scope of the present disclosure encompasses substrate support that define cells of other shapes, such as square, rectangular, and the like.

The term "catalyst" is used in accordance with its plain ordinary meaning and refers to a substance that modulates (e.g., increases the rate of a chemical reaction relative to the absence of the catalyst) the rate of a chemical reaction without being consumed in the reaction. In embodiments, the catalyst is a methanation catalyst.

The term "substrate support" as used herein refers to a material (e.g., a solid material) to which a catalyst is affixed and/or incorporated. In embodiments, the catalyst is covalently bound to the substrate support. Typically substrate supports have high BET surface area and are inert in the catalytic reactions. A substrate support may be a particle (e.g., nanoparticle or microparticle). In embodiments, the substrate support is ceramic. Non-limiting examples of substrate supports are comprised of ceramic, olivine, dolomite, calcium carbonate, aluminum oxide, silicon dioxide, titanium dioxide, and iron oxide. In embodiments, the substrate support comprises aluminum oxide, silicon dioxide, titanium dioxide, and iron oxide (e.g., Carbo HSP). In embodiments, the substrate support is sintered bauxite. In embodiments, the substrate support is cordierite. In embodiments, the substrate support is alumina (e.g., $Al_2O_3$).

The term "impregnated" as used herein refers to a state of being soaked or saturated with a substance. In embodiments, catalysts were prepared by wet-impregnation method on substrate support.

The term "low BET surface area support" as used herein refers to a material with low BET surface area support. In embodiments, the low BET surface area support is alumina support. In embodiments, the low BET surface area alumina support is CoorsTek AD90 $Al_2O_3$.

The term "high BET surface area support" as used herein refers to a material with high BET surface area support. In embodiments, the high BET surface area support is alumina support. In embodiments, the high BET surface area alumina support is Delta AA400G $Al_2O_3$. In embodiments, the high BET surface area alumina support is Sasol PURALOX 300/200 $Al_2O_3$.

The term "calcination temperature" as used herein refers to the temperature at which the catalyst is thermally treated in an oxidizing atmosphere, generally air A "nanoparticle," as used herein, is a particle wherein the longest diameter is less than or equal to 1000 nanometers. Nanoparticles may be composed of any appropriate material. For example, nanoparticle cores may include appropriate metals and metal oxides thereof (e.g., a metal nanoparticle core), carbon (e.g., an organic nanoparticle core) silicon and oxides thereof (e.g., a silicon nanoparticle core) or boron and oxides thereof (e.g., a boron nanoparticle core), or mixtures thereof. The nanoparticle may be a metal nanoparticle. When the nanoparticle is a metal, the metal may be titanium, zirconium, gold, silver, platinum, cerium, arsenic, iron, aluminum or silicon. The metal nanoparticle may be titanium, zirconium, gold, silver, or platinum and appropriate metal oxides thereof. In embodiments, the nanoparticle is titanium oxide, zirconium oxide, cerium oxide, arsenic oxide, iron oxide, aluminum oxide, or silicon oxide.

A "microparticle," as used herein, is a particle wherein the longest diameter is less than or equal to 1000 micrometers, and greater than 1000 nanometers. Microparticles may be composed of any appropriate material. For example, microparticle cores may include appropriate metals and metal oxides thereof (e.g., a metal microparticle core), carbon (e.g., an organic microparticle core) silicon and oxides thereof (e.g., a silicon microparticle core) or boron and oxides thereof (e.g., a boron microparticle core), or mixtures thereof. The microparticle may be a metal microparticle. When the microparticle is a metal, the metal may be titanium, zirconium, gold, silver, platinum, cerium, arsenic, iron, aluminum or silicon. The metal microparticle may be titanium, zirconium, gold, silver, or platinum and appropriate metal oxides thereof. In embodiments, the microparticle is titanium oxide, zirconium oxide, cerium oxide, arsenic oxide, iron oxide, aluminum oxide, or silicon oxide.

The term "tar" and "condensable hydrocarbons" are used synonymously and are used in accordance with their plain ordinary meaning in the art and refers to organic compounds with a molecular mass greater than benzene which condense on metal surfaces at room temperature. Tar is formed during gasification, the exact composition of which depends on the reaction conditions.

The term "contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a compound as described herein and a catalyst or substrate support.

It is understood that the weight percent (i.e. wt %) of the catalyst should be equal to 100% when summing the % wt of the individual components, (e.g. nickel, ruthenium, and magnesium dioxide; nickel and ruthenium; nickel, ruthenium, magnesium dioxide, and the substrate support). In embodiments, the wt % is calculated as the sum of the individual components, e.g. nickel, ruthenium, and magnesium oxide and the substrate support. In embodiments the wt % does not include the substrate support. In embodiments, the weight percent of the catalyst is calculated by summing two of the three components (e.g., Ni and Ru), such that the catalyst Ni95Ru05 refers to a catalyst including 95 wt % Ni and 5 wt % Ruthenium.

II. Catalyst Compositions

In an aspect, provided is a catalyst comprising nickel (Ni), magnesium oxide (MgO), and ruthenium (Ru). In embodiments, the catalyst includes about 10 to 95 wt % Ni. In embodiments, the catalyst includes about 0.5 to 5.0 wt % MgO. In embodiments, the catalyst includes about 0.5 to 5 wt % Ru.

In embodiments, the catalyst includes about 1 to about 95 wt % Ni. In embodiments, the catalyst includes about 5 to about 95 wt % Ni. In embodiments, the catalyst includes about 10 to about 95 wt % Ni. In embodiments, the catalyst includes about 15 to about 90 wt % Ni. In embodiments, the catalyst includes about 20 to about 85 wt % Ni. In embodiments, the catalyst includes about 25 to about 80 wt % Ni. In embodiments, the catalyst includes about 30 to about 75 wt % Ni. In embodiments, the catalyst includes about 35 to about 70 wt % Ni. In embodiments, the catalyst includes about 40 to about 65 wt % Ni. In embodiments, the catalyst includes about 45 to about 60 wt % Ni. In embodiments, the catalyst includes about 50 to about 55 wt % Ni. In embodiments, the catalyst includes about 50 to 50 wt % Ni. In embodiments, the catalyst includes about 1 wt % Ni. In embodiments, the catalyst includes about 5 wt % Ni. In embodiments, the catalyst includes about 10 wt % Ni. In embodiments, the catalyst includes about 15 wt % Ni. In embodiments, the catalyst includes about 20 wt % Ni. In embodiments, the catalyst includes about 25 wt % Ni. In embodiments, the catalyst includes about 30 wt % Ni. In embodiments, the catalyst includes about 35 wt % Ni. In embodiments, the catalyst includes about 40 wt % Ni. In embodiments, the catalyst includes about 45 wt % Ni. In embodiments, the catalyst includes about 50 wt % Ni. In embodiments, the catalyst includes about 55 wt % Ni. In embodiments, the catalyst includes about 60 wt % Ni. In embodiments, the catalyst includes about 65 wt % Ni. In embodiments, the catalyst includes about 70 wt % Ni. In embodiments, the catalyst includes about 75 wt % Ni. In embodiments, the catalyst includes about 80 wt % Ni. In embodiments, the catalyst includes about 85 wt % Ni. In embodiments, the catalyst includes about 90 wt % Ni. In embodiments, the catalyst includes about 95 wt % Ni.

In embodiments, the catalyst includes about 0.1 to about 10.0 wt % MgO. In embodiments, the catalyst includes about 0.2 to about 8.0 wt % MgO. In embodiments, the catalyst includes about 0.3 to about 7.0 wt % MgO. In embodiments, the catalyst includes about 0.4 to about 6.0 wt % MgO. In embodiments, the catalyst includes about 0.5 to about 5.0 wt % MgO. In embodiments, the catalyst includes about 0.6 to about 4.0 wt % MgO. In embodiments, the catalyst includes about 0.7 to about 3.0 wt % MgO. In embodiments, the catalyst includes about 0.8 to about 2.0 wt % MgO. In embodiments, the catalyst includes about 0.9 to about 1.0 wt % MgO. In embodiments, the catalyst includes about 0.1 wt % MgO. In embodiments, the catalyst includes about 0.2 wt % MgO. In embodiments, the catalyst includes about 0.3 wt % MgO. In embodiments, the catalyst includes about 0.4 wt % MgO. In embodiments, the catalyst includes about 0.5 wt % MgO. In embodiments, the catalyst includes about 0.6 wt % MgO. In embodiments, the catalyst includes about 0.7 wt % MgO. In embodiments, the catalyst includes about 0.8 wt % MgO. In embodiments, the catalyst includes about 0.9 wt % MgO. In embodiments, the catalyst includes about 1.0 wt % MgO. In embodiments, the catalyst includes about 2.0 wt % MgO. In embodiments, the catalyst includes about 3.0 wt % MgO. In embodiments, the catalyst includes about 4.0 wt % MgO. In embodiments, the catalyst includes about 5.0 wt % MgO. In embodiments, the catalyst includes about 6.0 wt % MgO. In embodiments, the catalyst includes about 7.0 wt % MgO. In embodiments, the catalyst includes about 8.0 wt % MgO. In embodiments, the catalyst includes about 9.0 wt % MgO. In embodiments, the catalyst includes about 10.0 wt % MgO.

In embodiments, the catalyst includes about 0.1 to about 10.0 wt % Ru. In embodiments, the catalyst includes about 0.2 to about 8.0 wt % Ru. In embodiments, the catalyst includes about 0.3 to about 7.0 wt % Ru. In embodiments, the catalyst includes about 0.4 to about 6.0 wt % Ru. In embodiments, the catalyst includes about 0.5 to about 5.0 wt % Ru. In embodiments, the catalyst includes about 0.6 to about 4.0 wt % Ru. In embodiments, the catalyst includes about 0.7 to about 3.0 wt % Ru. In embodiments, the catalyst includes about 0.8 to about 2.0 wt % Ru. In embodiments, the catalyst includes about 0.9 to about 1.0 wt % Ru. In embodiments, the catalyst includes about 0.1 wt % Ru. In embodiments, the catalyst includes about 0.2 wt % Ru. In embodiments, the catalyst includes about 0.3 wt % Ru. In embodiments, the catalyst includes about 0.4 wt % Ru. In embodiments, the catalyst includes about 0.5 wt % Ru. In embodiments, the catalyst includes about 0.6 wt % Ru. In embodiments, the catalyst includes about 0.7 wt % Ru. In embodiments, the catalyst includes about 0.8 wt % Ru. In embodiments, the catalyst includes about 0.9 wt % Ru. In embodiments, the catalyst includes about 1.0 wt % Ru. In embodiments, the catalyst includes about 2.0 wt % Ru. In embodiments, the catalyst includes about 3.0 wt % Ru. In embodiments, the catalyst includes about 4.0 wt % Ru. In embodiments, the catalyst includes about 5.0 wt % Ru. In embodiments, the catalyst includes about 6.0 wt % Ru. In embodiments, the catalyst includes about 7.0 wt % Ru. In embodiments, the catalyst includes about 8.0 wt % Ru. In embodiments, the catalyst includes about 9.0 wt % Ru. In embodiments, the catalyst includes about 10.0 wt % Ru.

In embodiments, the loading of Ni is fixed at about 10% in all catalysts. In embodiments, the loading of Ru and MgO is optimized to obtain the highest activity and $CH_4$ selectivity.

In an aspect, provided is a catalyst comprising nickel (Ni) and ruthenium (Ru). In embodiments, the Ni:Ru weight ratio is about 95:5 to about 90:10. In embodiments, the Ni:Ru weight ratio is about 90:10. In embodiments, the Ni:Ru weight ratio is about 91:9. In embodiments, the Ni:Ru weight ratio is about 92:8. In embodiments, the Ni:Ru weight ratio is about 93:7. In embodiments, the Ni:Ru weight ratio is about 94:6. In embodiments, the Ni:Ru weight ratio is about 95:5. In embodiments, catalyst includes about 1.5 wt % MgO.

In embodiments, the catalyst includes about 1.5 wt % MgO, about 9.5 wt % Ni, and about 0.5 wt % Ru; whereby the wt % of the substrate support is about 88.5 wt %. In embodiments, the catalyst includes about 1.5 wt % MgO, about 9 wt % Ni, and about 1 wt % Ru; whereby the wt % of the substrate support is about 88.5 wt %. In embodiments, the catalyst includes about 1.5 wt % MgO, about 8.5 wt % Ni, and about 1.5 wt % Ru; whereby the wt % of the substrate support is about 88.5 wt %. In embodiments, the catalyst includes about 1.5 wt % MgO, about 8 wt % Ni, and about 2 wt % Ru; whereby the wt % of the substrate support is about 88.5 wt %. In embodiments, the catalyst includes about 1.5 wt % MgO, about 7.5 wt % Ni, and about 2.5 wt % Ru; whereby the wt % of the substrate support is about 88.5 wt %. In embodiments, the catalyst includes about 1.5 wt % MgO, about 7 wt % Ni, and about 3 wt % Ru; whereby the wt % of the substrate support is about 88.5 wt %. In embodiments, the catalyst includes about 1.5 wt % MgO, about 6.5 wt % Ni, and about 3.5 wt % Ru; whereby the wt % of the substrate support is about 88.5 wt %. In embodiments, the catalyst includes about 1.5 wt % MgO, about 6 wt % Ni, and about 4 wt % Ru; whereby the wt % of the substrate support is about 88.5 wt %. In embodiments, the catalyst includes about 1.5 wt % MgO, about 5.5 wt % Ni, and about 4.5 wt % Ru; whereby the wt % of the substrate support is about 88.5 wt %. In embodiments, the catalyst includes about 1.5 wt % MgO, about 5 wt % Ni, and about 5 wt % Ru; whereby the wt % of the substrate support is about 88.5 wt %.

In embodiments, the catalyst further comprises a substrate support. In embodiments, the substrate support comprises ceramic, olivine, dolomite, calcium carbonate, aluminum oxide, silicon dioxide, titanium dioxide, or iron oxide. In embodiments, the substrate support is $Al_2O_3$. In embodiments, the $Al_2O_3$ substrate support is a low BET surface area substrate support. In embodiments, the $Al_2O_3$ low BET surface area substrate support is CoorsTek AD90. In embodiments, CoorsTek AD90 has the BET surface area of ~0.62 $m^2/g$. In embodiments, CoorsTek AD90 has the BET surface area of from 1.2 to 4.5 $m^2/g$.

In embodiments, the $Al_2O_3$ substrate support is a high BET surface area support. In embodiments, the $Al_2O_3$ high BET surface area substrate support is Delta AA400G. In embodiments, Delta AA400G has the BET surface area of from 82.4 to 86.3 $m^2/g$. In embodiments, the $Al_2O_3$ high BET surface area substrate support is Sasol (PURALOX 300/200). In embodiments, Sasol (PURALOX 300/200) has the BET surface area of ~106 $m^2/g$.

In embodiments, the catalyst to substrate support weight ratio is about 5.0 to about 30.0. In embodiments, the catalyst to substrate support weight ratio is about 10.0 to about 25.0. In embodiments, the catalyst to substrate support weight ratio is about 15.0 to about 20.0. In embodiments, the catalyst to substrate support weight ratio is about 5.0 to about 20.0. In embodiments, the catalyst to substrate support weight ratio is about 10.0. In embodiments, the catalyst to substrate support weight ratio is about 15.0. In embodiments, the catalyst to substrate support weight ratio is about 20.0. In embodiments, the catalyst to substrate support weight ratio is about 25.0. In embodiments, the catalyst to substrate support weight ratio is about 30.0.

In embodiments, the loading of Ni is fixed at about 10 wt % in all catalysts. In embodiments, the loading of Ru and MgO is optimized to obtain the highest activity and $CH_4$ selectivity. In embodiments, the catalyst is about 10 wt % Ni, about 1.5 wt % MgO+about 10 wt % Ni. In embodiments, the catalyst is about 1.5 wt % MgO+about 9.5 wt % Ni+about 0.5 wt % Ru. In embodiments, the catalyst is about 1.5 wt % MgO+about 9 wt % Ni+about 1 wt % Ru. The detailed elemental loadings with catalyst compositions are presented in Table 1. In embodiments, the catalyst is a catalyst as described herein (e.g., in Table 1 or Table 2).

III. Methods of Making and Use

In an aspect, provided is a method of making a nickel-magnesium oxide-ruthenium catalyst, (e.g., a catalyst as described herein), wherein the method includes (a) mixing nickel nitrate, magnesium nitrate, ruthenium chloride in a solvent; (b) combining the solution of step (a) with a substrate support to form a mixture; and maintaining the mixture of step (b) at a constant temperature for at least 12 hours. In embodiments, a nickel-magnesium oxide-ruthenium catalyst is prepared by wet impregnation. In embodiments, a nickel-magnesium oxide-ruthenium catalyst is prepared by wet impregnation on a $Al_2O_3$ support. In embodiments, the mixture of step (b) is maintained for about 12 hours at 100° C. and for about 3 hours at 500° C. In embodiments, the method is described herein, e.g., in Experimental methods and Examples 1 to 4.

In an aspect, provided herein is a method of making a nickel-magnesium oxide-ruthenium catalyst, (e.g., a catalyst as described herein) on a low BET surface area support, wherein the method includes (a) mixing nickel nitrate, magnesium nitrate, ruthenium chloride in a solvent; (b) combining the solution of step (a) with a substrate support to form a mixture; and maintaining the mixture of step (b) at a constant temperature for at least 12 hours. In embodiments, the mixture of step (b) is maintained for about 12 hours at 100° C. and for about 3 hours at 500° C. In embodiments, the method is described herein, e.g., in Experimental methods and Examples 1 to 3.

In embodiments, the low BET surface area support is $Al_2O_3$ support. In embodiments, the $Al_2O_3$ support is CoorsTek AD90. In embodiments, CoorsTek AD90 has the BET surface area of ~0.62 $m^2/g$. In embodiments, CoorsTek AD90 has the BET surface area of from 1.2 to 4.5 $m^2/g$.

In embodiments, the mixture is dried at a temperature of about 90° C. to about 150° C. In embodiments, the mixture is dried at a temperature of about 95° C. to about 145° C. In embodiments, the mixture is dried at a temperature of about 100° C. to about 140° C. In embodiments, the mixture is dried at a temperature of about 105° C. to about 135° C. In embodiments, the mixture is dried at a temperature of about 110° C. to about 130° C. In embodiments, the mixture is dried at a temperature of about 115° C. to about 125° C. In embodiments, the mixture is dried at a temperature of about 90° C. In embodiments, the mixture is dried at a temperature of about 95° C. In embodiments, the mixture is dried at a temperature of about 100° C. In embodiments, the mixture is dried at a temperature of about 105° C. In embodiments, the mixture is dried at a temperature of about 110° C. In embodiments, the mixture is dried at a temperature of about 115° C. In embodiments, the mixture is dried at a temperature of about 120° C. In embodiments, the mixture is dried at a temperature of about 125° C. In embodiments, the mixture is dried at a temperature of about 130° C. In embodiments, the mixture is dried at a temperature of about 135° C. In embodiments, the mixture is dried at a temperature of about 140° C. In embodiments, the mixture is dried at a temperature of about 145° C. In embodiments, the mixture is dried at a temperature of about 150° C.

In embodiments, the temperature in increased at an interval of about 10° C. to about 100° C. after the mixture is dried. In embodiments, the temperature in increased at an interval of about 15° C. to about 95° C. after the mixture is dried. In embodiments, the temperature in increased at an interval of about 20° C. to about 80° C. after the mixture is dried. In embodiments, the temperature in increased at an interval of about 25° C. to about 75° C. after the mixture is dried. In embodiments, the temperature in increased at an interval of about 30° C. to about 70° C. after the mixture is dried. In embodiments, the temperature in increased at an interval of about 35° C. to about 65° C. after the mixture is dried. In embodiments, the temperature in increased at an interval of about 40° C. to about 60° C. after the mixture is dried. In embodiments, the temperature in increased at an interval of about 45° C. to about 55° C. after the mixture is dried. In embodiments, the temperature in increased at an interval of about 10° C. after the mixture is dried. In embodiments, the temperature in increased at an interval of about 15° C. after the mixture is dried. In embodiments, the temperature in increased at an interval of about 20° C. after the mixture is dried. In embodiments, the temperature in increased at an interval of about 25° C. after the mixture is dried. In embodiments, the temperature in increased at an interval of about 30° C. after the mixture is dried. In embodiments, the temperature in increased at an interval of about 35° C. after the mixture is dried. In embodiments, the temperature in increased at an interval of about 40° C. after the mixture is dried. In embodiments, the temperature in increased at an interval of about 45° C. after the mixture is dried. In embodiments, the temperature in increased at an interval of about 50° C. after the mixture is dried. In embodiments, the temperature in increased at an interval of about 55° C. after the mixture is dried. In embodiments, the temperature in increased at an interval of about 60° C. after the mixture is dried. In embodiments, the temperature in increased at an interval of about 65° C. after the mixture is dried. In embodiments, the temperature in increased at an interval of about 70° C. after the mixture is dried. In embodiments, the temperature in increased at an interval of about 75° C. after the mixture is dried. In embodiments, the temperature in increased at an interval of about 80° C. after the mixture is dried. In embodiments, the temperature in increased at an interval of about 85° C. after the mixture is dried. In embodiments, the temperature in increased at an interval of about 90° C. after the mixture is dried. In embodiments, the temperature in increased at an interval of about 95° C. after the mixture is dried. In embodiments, the temperature in increased at an interval of about 100° C. after the mixture is dried.

In embodiments, the temperature in increased up to about 500° C. after the mixture is dried. In embodiments, the temperature in increased up to about 525° C. after the mixture is dried. In embodiments, the temperature in increased up to about 550° C. after the mixture is dried. In embodiments, the temperature in increased up to about 575° C. after the mixture is dried. In embodiments, the temperature in increased up to about 600° C. after the mixture is dried. In embodiments, the temperature in increased up to about 625° C. after the mixture is dried. In embodiments, the temperature in increased up to about 650° C. after the mixture is dried. In embodiments, the temperature in increased up to about 675° C. after the mixture is dried. In embodiments, the temperature in increased up to about 700° C. after the mixture is dried. In embodiments, the temperature in increased up to about 725° C. after the mixture is dried. In embodiments, the temperature in increased up to about 750° C. after the mixture is dried.

In embodiments, the mixture is maintained at the calcination temperature for about 1 h. In embodiments, the mixture is maintained at the calcination temperature for about 1.5 h. In embodiments, the mixture is maintained at the calcination temperature for about 2 h. In embodiments, the mixture is maintained at the calcination temperature for about 2.5 h. In embodiments, the mixture is maintained at the calcination temperature for about 3 h. In embodiments, the mixture is maintained at the calcination temperature for about 3.5 h. In embodiments, the mixture is maintained at the calcination temperature for about 4 h. In embodiments, the mixture is maintained at the calcination temperature for about 4.5 h. In embodiments, the mixture is maintained at the calcination temperature for about 5 h. In embodiments, the mixture is maintained at the calcination temperature for about 5.5 h. In embodiments, the mixture is maintained at the calcination temperature for about 6 h. In embodiments, the mixture is maintained at the calcination temperature for about 6.5 h. In embodiments, the mixture is maintained at the calcination temperature for about 7 h. In embodiments, the mixture is maintained at the calcination temperature for about 7.5 h.

In an aspect, provided herein is a method of making a nickel-magnesium oxide-ruthenium catalyst, (e.g., a catalyst as described herein) on a high BET surface area support, wherein the method includes (a) mixing nickel nitrate, magnesium nitrate, ruthenium chloride in a solvent; (b) combining the solution of step (a) with a substrate support to form a mixture; and maintaining the mixture of step (b) at a constant temperature for at least 12 hours. In embodiments, the method is described herein, e.g., in Example 4.

In embodiments, the high BET surface area substrate support is $Al_2O_3$ substrate support. In embodiments, the $Al_2O_3$ high BET surface area substrate support is Delta AA400G. In embodiments, the Delta AA400G has the BET surface area from 82.4 to 86.3 $m^2/g$. In embodiments, the $Al_2O_3$ high BET surface area substrate support is Sasol (PURALOX 300/200). In embodiments, the Sasol (PURALOX 300/200) has the BET surface area of ~106 $m^2/g$.

In embodiments, the catalytic reaction is performed in a fixed-bed reactor. In embodiments, the fixed-bed reactor employs a 10 mm inner diameter quartz-tube reactor.

In embodiments, a total $H_2$ flow rate is about 300 to about 500 sccm. In embodiments, a total $H_2$ flow rate is about 325 to about 475 sccm. In embodiments, a total $H_2$ flow rate is about 350 to about 450 sccm. In embodiments, a total $H_2$ flow rate is about 375 to about 425 sccm. In embodiments, a total $H_2$ flow rate is about 300 sccm. In embodiments, a total $H_2$ flow rate is about 325 sccm. In embodiments, a total $H_2$ flow rate is about 350 sccm. In embodiments, a total $H_2$ flow rate is about 375 sccm. In embodiments, a total $H_2$ flow rate is about 400 sccm. In embodiments, a total $H_2$ flow rate is about 425 sccm. In embodiments, a total $H_2$ flow rate is about 450 sccm. In embodiments, a total $H_2$ flow rate is about 475 sccm. In embodiments, a total $H_2$ flow rate is about 500 sccm.

In embodiments, the reaction temperature is between about 250° C. and about 500° C. In embodiments, the reaction temperature is between about 275° C. and about 475° C. In embodiments, the reaction temperature is between about 300° C. and about 450° C. In embodiments, the reaction temperature is between about 325° C. and about 425° C. In embodiments, the reaction temperature is between about 350° C. and about 400° C. In embodiments, the reaction temperature is about 250° C. In embodiments, the reaction temperature is about 275° C. In embodiments, the reaction temperature is about 300° C. In embodiments, the reaction temperature is about 325° C. In embodiments, the reaction temperature is about 350° C. In embodiments, the reaction temperature is about 375° C. In embodiments, the reaction temperature is about 400° C. In embodiments, the reaction temperature is about 425° C. In embodiments, the reaction temperature is about 450° C. In embodiments, the reaction temperature is about 475° C. In embodiments, the reaction temperature is about 500° C.

In embodiments, the catalyst particles size is about 354 µM to about 430 µM when the Delta AA400G support is used. In embodiments, the catalyst particles size is about 345 µM to about 376 µM when the Sasol support is used.

In embodiments, a high BET surface area substrate support provides an increased catalyst loading. In embodiments, a catalyst loading is about 10 wt % to about 50 wt %. In embodiments, a catalyst loading is about 15 wt % to about 45 wt %. In embodiments, a catalyst loading is about 20 wt % to about 40 wt %. In embodiments, a catalyst loading is about 25 wt % to about 35 wt %. In embodiments, a catalyst loading is about 10 wt %. In embodiments, a catalyst loading is about 15 wt %. In embodiments, a catalyst loading is about 20 wt %. In embodiments, a catalyst loading is about 25 wt %. In embodiments, a catalyst loading is about 30 wt %. In embodiments, a catalyst loading is about 35 wt %. In embodiments, a catalyst loading is about 40 wt %. In embodiments, a catalyst loading is about 45 wt %. In embodiments, a catalyst loading is about 50 wt %.

In an aspect, provided is a method of converting gas mixture to methane, said method comprising contacting the catalyst (e.g., a catalyst as described herein, including embodiments) with the gas mixture, wherein said gas mixture includes CO, $CO_2$, and $H_2$. In embodiments, the gas mixture further includes water.

In embodiments, CO conversion is about 10% to about 100%. In embodiments, CO conversion is about 15% to about 95%. In embodiments, CO conversion is about 20% to about 90%. In embodiments, CO conversion is about 25% to about 85%. In embodiments, CO conversion is about 30% to about 80%. In embodiments, CO conversion is about 35% to about 75%. In embodiments, CO conversion is about 40% to about 70%. In embodiments, CO conversion is about 45% to about 65%. In embodiments, CO conversion is about 50% to about 60%. In embodiments, CO conversion is about 10%. In embodiments, CO conversion is about 15%. In embodiments, CO conversion is about 20%. In embodiments, CO conversion is about 25%. In embodiments, CO conversion is about 30%. In embodiments, CO conversion is about 35%. In embodiments, CO conversion is about 40%. In embodiments, CO conversion is about 45%. In embodiments, CO conversion is about 50%. In embodiments, CO conversion is about 55%. In embodiments, CO conversion is about 60%. In embodiments, CO conversion is about 65%. In embodiments, CO conversion is about 70%. In embodiments, CO conversion is about 75%. In embodiments, CO conversion is about 80%. In embodiments, CO conversion is about 85%. In embodiments, CO conversion is about 90%. In embodiments, CO conversion is about 95%. In embodiments, CO conversion is about 100%.

In embodiments, the catalyst, as described herein, displays no deactivation up to about 78 hours. In embodiments, the commercial catalyst displays significant deactivation.

In embodiments, the catalyst, as described herein, displays a minimal drop in CO conversion after 78 hours. In embodiments, the commercial catalyst displays a drop in CO conversion from about 96% to about 60% after 48 hours.

The use of higher BET surface area catalyst supports, such as Delta AA400G and Sasol PURALOX 300/200, substantially increased performance of the Mg—NiRu catalyst at lower temperatures. The Mg—NiRu catalyst demonstrated superior performance with respect to deactivation by coke formation.

Embodiments

Embodiment 1. A catalyst comprising nickel (Ni), magnesium oxide (MgO), and ruthenium (Ru), wherein the catalyst comprises about 10 to about 95 wt % Ni; about 0.5 to about 5.0 wt % MgO; and about 0.5 to about 5 wt % Ru.

Embodiment 2. The catalyst of embodiment 1, wherein the Ni:Ru weight ratio is about 95:5 to about 90:10.

Embodiment 3. The catalyst of embodiment 1 or 2, wherein the catalyst further comprises a substrate support.

Embodiment 4. The catalyst of any one of embodiments 1 to 3, wherein the substrate support comprises ceramic, olivine, dolomite, calcium carbonate, aluminum oxide, silicon dioxide, titanium dioxide, or iron oxide.

Embodiment 5. The catalyst of any one of embodiments 1 to 4, wherein the substrate support is a low BET surface area aluminum oxide.

Embodiment 6. The catalyst of any one of embodiments 1 to 5, wherein the substrate support is a high BET surface area aluminum oxide.

Embodiment 7. The catalyst of any one of embodiments 1 to 6, wherein the catalyst to substrate support weight ratio is about 5.0 to about 30.0.

Embodiment 8. A method of making a nickel-magnesium oxide-ruthenium catalyst, said method comprising:
(a) mixing nickel nitrate, magnesium nitrate, ruthenium chloride in a solvent;
(b) combining the solution of step (a) with a substrate support to form a mixture; and
(c) maintaining the mixture of step (b) at a constant temperature for at least 12 hours.

Embodiment 9. The method of embodiment 8, wherein the substrate support is a low BET surface area aluminum oxide support.

Embodiment 10. The method of embodiment 8, wherein the substrate support is a high BET surface area aluminum oxide support.

Embodiment 11. A method of converting gas mixture to methane, said method comprising contacting the catalyst of claim 1 with the gas mixture, wherein said gas mixture comprises CO, $CO_2$, and $H_2$.

Embodiment 12. The method of embodiment 11, wherein the catalyst comprises the high BET surface area support aluminum oxide.

Embodiment 13. The method of embodiment 11 or 12, wherein the catalyst provides an increased CO conversion with an increased loading at a lower temperature.

Embodiment 14. The method of any one of embodiments 11 to 13, wherein the CO conversion is up to 95%.

Embodiment 15. The method of any one of embodiments 11 to 14, wherein the temperature is about 325° C.

EXAMPLES

Experimental Methods

The catalysts were prepared by wet-impregnation method on a $Al_2O_3$ support (CoorsTek, AD90) used for impregnating active catalyst components comprising of Ni, Mg—Ni and Mg—Ni—Ru. $Ni(NO_3)_2 \cdot 6H_2O$, $Mg(NO_3)_2 \cdot 6H_2O$ and $RuCl_3 \cdot xH_2O$ were used as precursors. Pre-calculated amount of the salts were combined into a water solution, and 20 g of support oxide were mixed to provide homogeneous wetting. The mixture was dried in an oven at 110° C. for 12 hrs and then the temperature was increased at an interval of 50° C. every 30 minutes up to 500° C. The samples were then maintained at the calcination temperature of 500° C. for 3 hrs.

The loading of Ni (or Ni+Ru) was fixed at 10 wt % in all catalysts. The loading of Ru and MgO was optimized to obtain the highest activity and $CH_4$ selectivity. The optimum compositions with MgO and Ru were named as Mg—Ni and Mg—NiRu. For example: 10% Ni, 1.5% MgO+10% Ni, 1.5% MgO+9.5% Ni+0.5% Ru, 1.5% MgO+9% Ni+1% Ru catalysts were represented as Ni, Mg—Ni, Mg—NiRu05 and Mg—NiRu10,

TABLE 1

Catalyst loading on AD 90 support, Nomenclature and BET surface area

| Catalyst | Component loading | | | Nomenclature used in the text | BET surface area ($m^2/g$) |
| --- | --- | --- | --- | --- | --- |
| | MgO (g) | Ni (g) | Ru (g) | | |
| CoorsTek AD 90 $Al_2O_3$ support (10 g basis) | | | | | |
| 10% Ni | — | 1.0 | — | | 1.2 |
| 9.5% Ni + 0.5% Ru | — | 0.95 | 0.05 | NiRu05 (or Ni95Ru05) | — |
| 9.0% Ni + 1.0% Ru | — | 0.9 | 0.1 | NiRu10 (or Ni90Ru10) | — |
| 1% MgO + 10% Ni | 0.1 | 1.0 | — | | — |
| 1.5% MgO + 10% Ni | 0.15 | 1.0 | — | Mg—Ni | 3.7 |
| 2% MgO + 10% Ni | 0.2 | 1.0 | — | | — |
| 3% MgO + 10% Ni | 0.3 | 1.0 | — | | — |
| 1.5% MgO + 10%(Ni95Ru05) | 0.15 | 0.95 | 0.05 | Mg—NiRu05 | 4.0 |
| 1.5%MgO + 10%(Ni90Ru10) | 0.15 | 0.9 | 0.1 | Mg—NiRu10 | 4.5 | respectively, in the following sections. The detailed elemental loadings with catalyst compositions are presented in Table 1.

X-ray diffraction (XRD) was performed with an X-ray diffractometer (BRUKER D2 PHASER) equipped with a monochromator for $CuK_\alpha$ radiation at a voltage of 30 kV, and a current of 100 mA. Samples were crushed to fine powders prior to measurement. During the measurement, samples were scanned from 2θ=20 to 60° at the rate of 0.02°/s. The observed patterns were identified using the International Centre for Diffraction Data (ICDD) database.

A copper grid coated with carbon and for-mava (polymer coated carbon grid used in TEM analysis) film were used to disperse the sample. The sample was prepared by placing few milligrams of fine powder (separated from alumina support surface) in spectral grade ethanol solution followed by ultra sonication.

Morphology and surface analysis of the catalysts were evaluated using field emission scanning electron microscope (FESEM, JEOL 7610F) and high resolution transmission electron microscope (JEOL JSM-2100F). For TEM analysis, a copper grid coated with carbon and for-mava (polymer coated carbon grid used in TEM analysis) film were used to disperse the sample. The sample was prepared by placing few milligrams of fine powder (separated from alumina support surface) in spectral grade ethanol solution followed by ultra sonication.

Nitrogen physisorption isotherms (adsorption-desorption branches) were measured on a Micromeritics ASAP 2020 instrument at 77 K. The samples were outgassed for 2 h under vacuum at 350° C. before measurement, and the specific surface area (SSA) was determined using the Brunauer Emmett Teller (BET) method. Temperature-programmed reduction (TPR) studies of the catalysts were performed to investigate the reduction behavior with a Quantachrome Instrument (ChemBET-3000 TPR/TPD). Typically, 500 mg of the sample was placed in a U-shaped quartz tube, and ramped from 40° C. to 700° C. at 10° C./min in a gas mixture containing $H_2$ and $N_2$. The consumption of $H_2$ during the reduction was monitored by a thermal conductivity detector (TCD). Prior to a TPR test, the sample was outgassed under inert-gas flow at 400° C. for 1 h.

The XPS analyses of Mg—Ni and Mg—NiRu catalysts were recorded using a SPECS spectrometer with non-monochromatic $AlK_\alpha$ radiation (1486.6 eV) as an X-ray source operated at 150 W (12.5 kV and 12 mA). All the spectra were obtained with a pass energy of 40 eV and a step increment of 0.05 eV. The CasaXPS program was employed for curve-fitting of the Ni2p core level spectra into several components with Gaussian-Lorenzian peaks after Shirley background subtraction. Peak positions, spin-orbit splitting, doublet intensity ratios, and full width at half maximum (FWHM) were fixed as given in the literature.

The catalytic reactions were investigated in a fixed-bed reactor using a 10 mm inner diameter quartz-tube reactor. Typically, 250 mg of the catalyst was mixed with quartz chips (1/32 inch) with a ratio of 1:20 (by wt.) and held in the reactor with quartz wool. The gas hourly space velocity (GHSV) was maintained at 96,000 cc $g^{-1}$ $h^{-1}$. The catalyst particles were mixed with the quartz diluent to maintain catalyst dispersion in order to mitigate heat-transfer limitations. The catalyst was reduced in-situ at 500° C. for 2 hrs under $H_2$ flow. Before the reduction step, the bed temperature was increased at 10° C. $min^{-1}$ under $N_2$ flow before it reached the target temperature. The reduction step is necessary to reduce oxides phases into active metallic phases. At the end of reduction, the reactor was cooled down under inert-gas flow. Experiments were performed at reaction temperatures between 350° C. and 475° C., and a total flow rate of 400 sccm. The actual temperature was 15 to 20° C. higher than the furnace set-point temperature. However, we report the set-point temperature, since actual temperature throughout the bed varied due to variation in catalyst concentration.

Methanation reactions were studied in two CO-containing gases: (i) Producer gas and (ii) $CO+H_2+N_2$ mixture. The inlet composition (mol %) of the producer-gas mixture (i) was: 40% H2, 8% CH4, 22% CO, 22% CO2, and 8% $N_2$. The second gas-mixture (ii) composition was: 40% H2, 22% CO, and 38% $N_2$. All the experimental data presented in this study were measured with multiple GC injections, and the averaged values are reported. The following expression was used to determine the activity of different catalysts.

The percent conversion for a reactant A is calculated by:

$$X_A(\%) = \left[\frac{mol_A^{in} - mol_A^{out}}{mol_A^{in}}\right] \times 100,$$

where $mol_A$ denotes the molar flow of reactant A in mol/s.

To determine the effect of high catalyst loading on high-surface-area catalyst supports, two commercial alumina catalysts supports were investigated: Delta AA400G and Sasol PURALOX 300/200. The detailed catalyst loadings are presented in Table 2. The high-surface-area catalysts were prepared with the previously described wet-impregnation method and experiments conducted over a range temperatures from 250° C. to 475° C. using producer gas.

Example 1. Ni—Ru—MgO Catalyst with High Activity and Stability for Methanation of CO+$H_2$ and Producer Gas A new methanation catalyst composition comprised of Ni, Ru and MgO was investigated. The catalysts were loaded on alumina support (CoorsTek, AD 90) by wet-impregnation method for testing the catalytic activity for CO+$H_2$ and producer gas in a fixed-bed reactor. The optimum loading of promoters including Ru and MgO with the parent Ni catalysts was determined by maximizing the CO conversion and $CH_4$ yield in the methanation reactions. The methanation activity as well as deactivation resistance of the catalyst were significantly improved as compared with Ni/Alumina or Ni—Ru/Alumina or Ni—MgO/Alumina. A 10% Ni loading achieved the highest activity and stability with addition of 1.5% MgO and 0.5-1.0% Ru as promoters. The optimization of MgO and Ru promoters was carried out on a low-surface-area alumina support developed for fluidized beds.

A standard commercial Ni-based methanation catalyst converts $CO_2$ with $H_2$ into $CH_4$. If CO is present in the $CO_2$ gas, the methanation catalyst deactivates and forms coke. The new catalyst formulation does not deactivate in the presence of CO and sustains a high activity for conversion of $CO_2$ and CO with $H_2$ into $CH_4$. Through a series of experiments, a systematic variation of composition of the catalyst was optimized for the synthesis of $CH_4$ from CO and $CO_2$.

Ni-XPS of pretreated Mg—Ni and Ni—Ru—Mg catalysts indicated presence of 30% Ni in metal form on the the $Al_2O_3$ support, although bulk reduction was found to be nearly 40% in the Mg—NiRu catalysts. The MgO promoter primarily enhanced the methanation activity, while the Ru component was mainly responsible for improvement in catalytic stability in the CO containing feed gas. The effect of $H_2O$ content in the feed gas showed no significant change in the methanation activity of the catalysts. Ni—Ru—Mg catalyst on low surface alumina support (AD 90) showed much higher stability as compared with other promoted Ni reference catalysts. It was observed that presence of CO was primarily responsible for catalyst deactivation due to coke formation. Thus, components of the new catalyst forms Ni—Ru—MgO to be used in methanation reactions.

Example 2. Catalytic Performance

Methanation of Producer Gas

The catalytic performance of the multi-component catalyst containing Ni, Ru, and MgO was optimized in composition to achieve the highest methanation activity and stability. The optimum content of the Ru and MgO promoters for the Ni catalyst was determined on a low-surface-area support by varying the concentration of the respective components by keeping total weight of Ni+Ru components constant at 10 wt %. In FIG. 1, a comparison of the methanation activity in producer gas over pure Ni, as well as Ru-promoted Ni catalysts, is presented. For these catalyst compositions, only CO methanation was observed in the producer gas, while $CO_2$ concentration remained unchanged. The presence of Ru led to higher conversion of CO on the Ni—Ru catalysts. For example: CO conversion at 450° C. was increased from 25% in Ni catalyst to 46% and 57% in NiRu05 and NiRu10 catalysts, respectively. The promotion by Ru can arise due to better dispersion of Ni in the catalysts or by enhancing $H_2$ adsorption on the catalyst surface.

Figure 2:
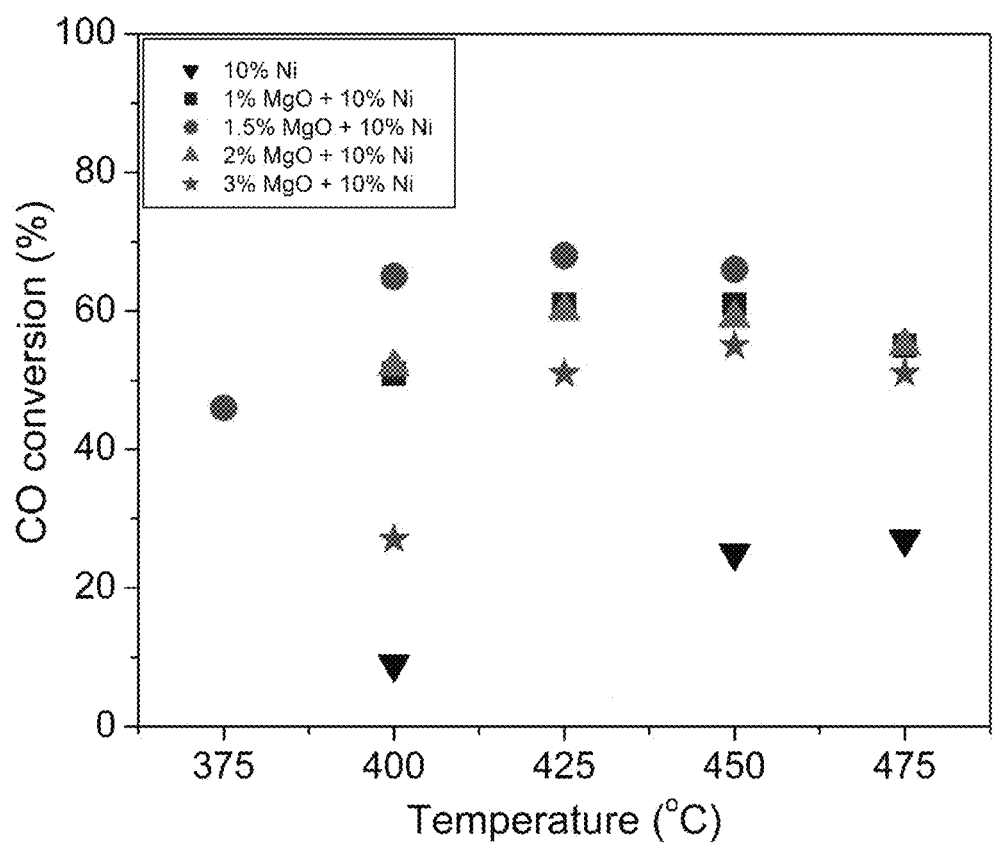
FIG. 2. Effect of MgO loading in Ni catalysts on Conversion of CO in producer gas; GHSV—96000 cc $g_{cat}^{-1}$ $h^{-1}$.

The conversion of CO in producer gas over 10% Ni catalyst, modified with increasing MgO content, is presented in FIG. 2. CO conversion is observed to be significantly enhanced by the addition of MgO as compared with pure Ni catalyst. The highest CO conversion was obtained at 1.5% MgO content and then decreased at higher loading. Since Ni cannot have an electronic interaction with non-reducible MgO, higher activity is attributed to enhanced dispersion of Ni particles. The decrease in activity at higher MgO loading may be due to strong interaction with NiO, availing less amount of active sites than calculated.

Figure 3:
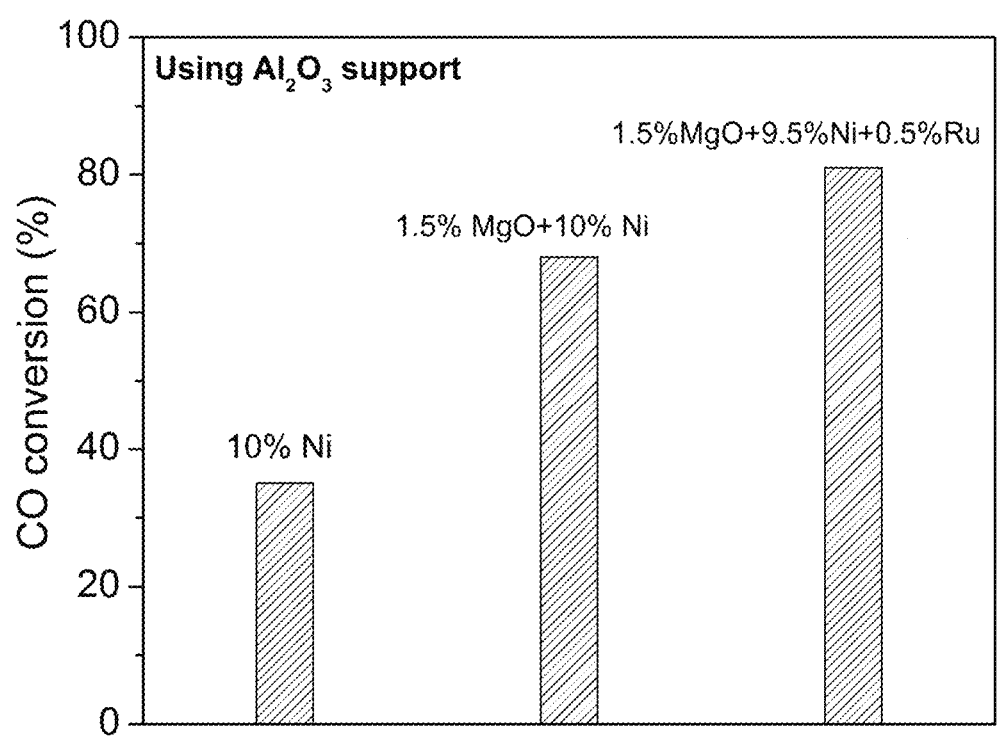
FIG. 3. A comparison of highest CO conversion in producer gas over pure Ni, Mg—Ni and Mg—NiRu05 catalysts; GHSV—96000 cc $g_{cat}^{-1}$ $h^{-1}$.
Figure 4:
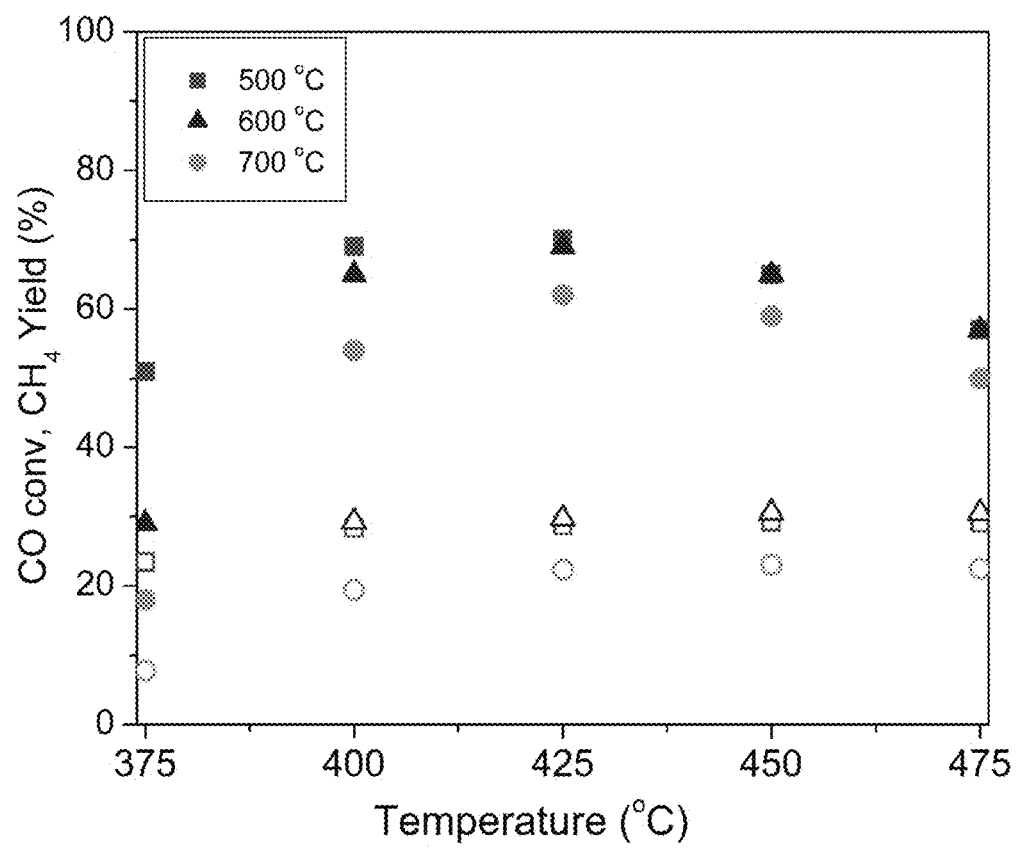
FIG. 4. Conversion of CO in producer gas over Mg—NiRu05 catalyst with pretreatment at different temperatures. GHSV—96000 cc $g_{cat}^{-1}$ $h^{-1}$ (Filled symbol—conversion, Empty symbol—$CH_4$ Yield).

The importance of the addition of both MgO and Ru as promoters to the Ni catalyst for enhancing methanation activity is presented in FIG. 3. The methanation activity is higher in Mg—NiRu05 catalyst due to the combined promoting effect of MgO and Ru of the Ni catalyst, as compared with MgO or Ru separately. However, the 1% Ru/$Al_2O_3$ composition did not show any methanation activity under this condition. The optimum methanation activity with the catalyst depends on the number of active sites on the surface. Since Ni forms a solid solution with MgO, formation of active sites may require higher temperature to form Ni crystallites. However, higher reduction temperatures could also lead to formation of larger particles, which can lead to a reduction in activity. Therefore, the methanation reactions over Mg—NiRu05 catalyst were investigated with calcining at different temperatures (FIG. 4). As shown in FIG. 4, both CO conversion and $CH_4$ yield are similar at calcination at 500° C. and 600° C., showing CO conversion and $CH_4$ yield of nearly 70% and 30%, respectively, at 425° C. The catalyst activity is slightly degraded by pre-treatment at 700° C. indicating larger particle formation.

The optimum methanation activity in the catalyst depends on the number of active sites on the surface. Since Ni forms a solid solution with MgO, formation of active sites may require higher temperature to form Ni crystallites. However, higher reduction temperature could also lead to formation of larger particles, which can lead to a reduction in activity. Therefore, methanation reactions over Mg—NiRu05 catalyst were carried out calcining at different temperatures (see FIG. 4). In the figure both CO conversion and $CH_4$ yield are similar with calcination at 500 and 600° C., showing CO conversion and $CH_4$ yield nearly 70% and 30%, respectively at 425° C. The catalyst activity is slightly degraded by pre-treatment at 700° C. indicating larger particle formation.

Figure 5:
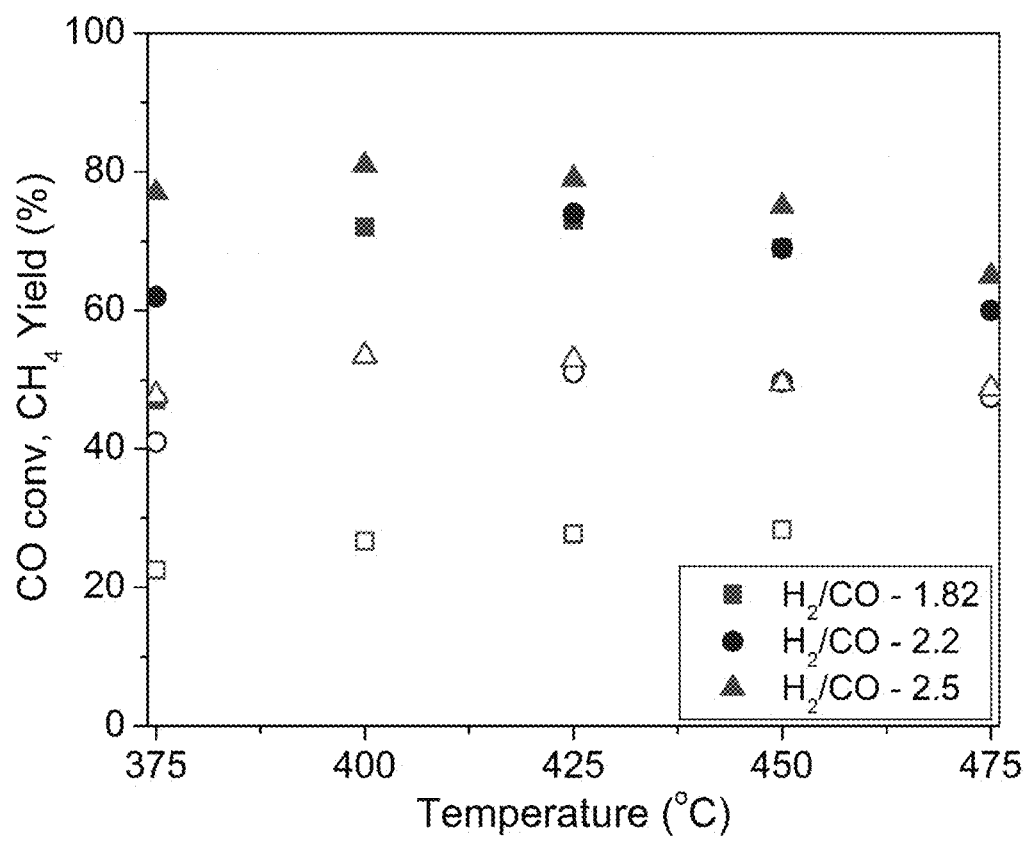
FIG. 5. CO conversion and $CH_4$ Yield with producer gas mixture varying $H_2$/CO ratios over Mg—NiRu05 catalyst (Filled symbol—conversion, Empty symbol—$CH_4$ Yield).

The performance of the methanation of producer gas with varying $H_2$/CO ratios over the Mg—NiRu05 catalyst is shown in FIG. 5. The $H_2$/CO ratio of the producer gas (1.8) was increased by adding additional hydrogen. The CO conversion is improved at lower temperature, down to 400° C. and improves slightly with increasing $H_2$/CO ratio. Selectivity is significantly improved by increasing the $H_2$/CO ratio from 1.82 to 2.2, and further improved on increasing to 2.5.

Figure 6:
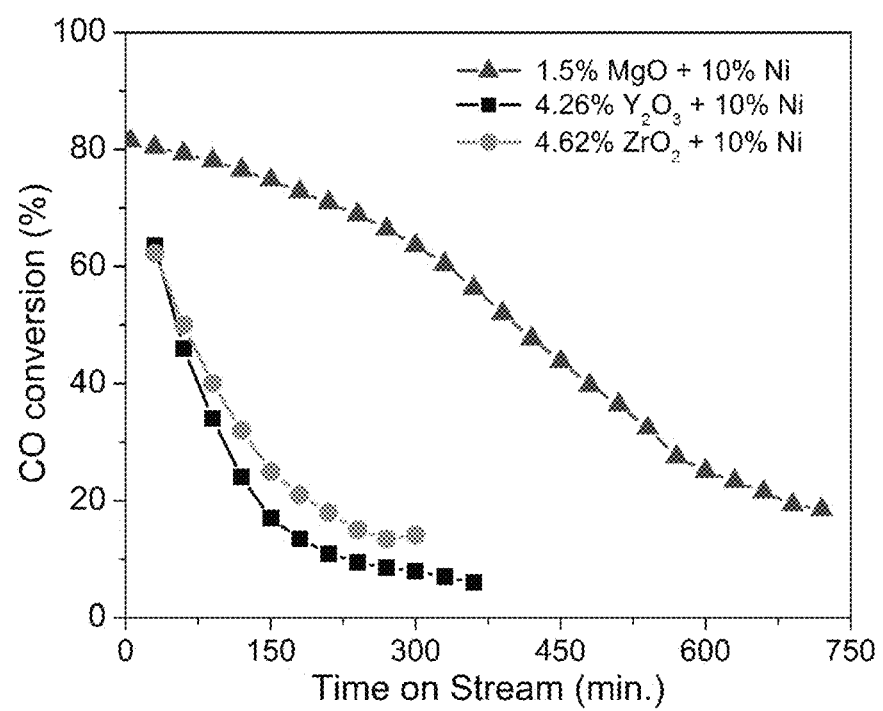
FIG. 6. A comparison of Time-on-Stream over MgO, $Y_2O_3$ and $ZrO_2$ promoted Ni catalysts for Methanation activity in producer gas mixture over at 425° C.; GHSV—96000 cc $g_{cat}^{-1}$ $h^{-1}$.

A comparison of methanation activity of MgO-promoted Ni with $Y_2O_3$— and $ZrO_2$— promoted Ni catalysts in producer gas is presented in FIG. 6. The rate of deactivation of MgO— promoted Ni is slower than the $Y_2O_3$— or $ZrO_2$-promoted analogs.

Figure 7:
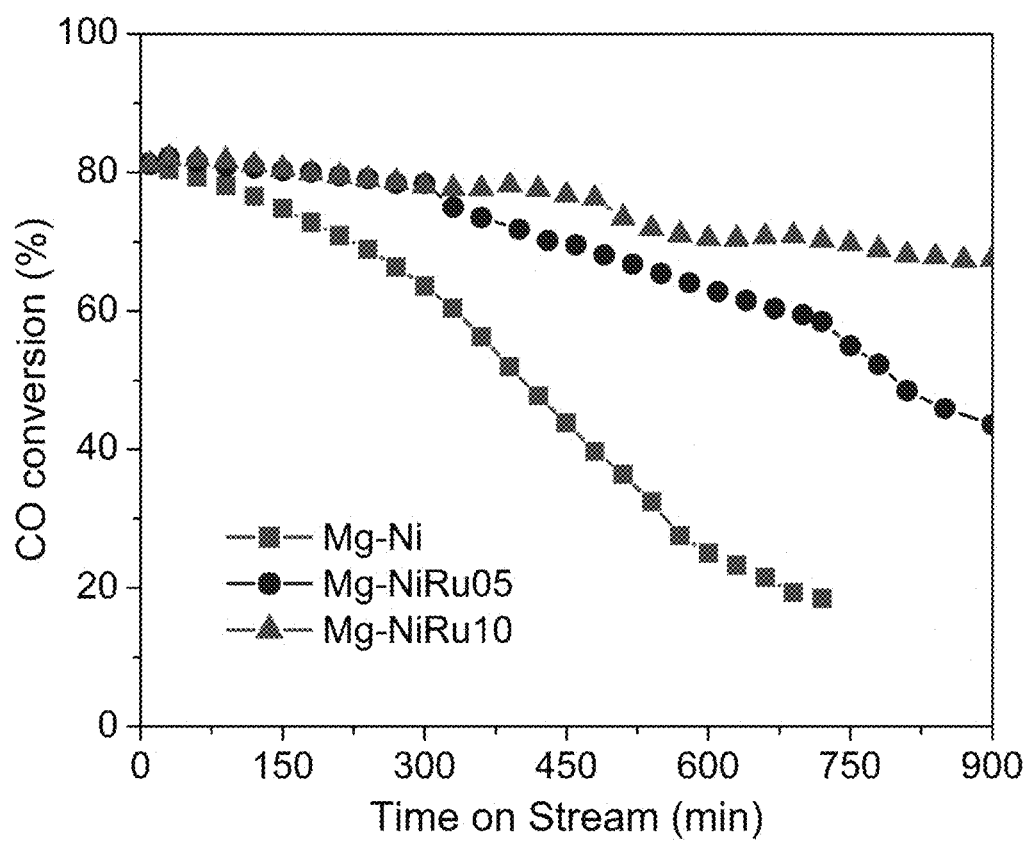
FIG. 7. Time-on-Stream for Methanation activity in producer gas mixture over Mg—Ni and Mg—NiRu catalysts at 425° C.; GHSV—96000 cc $g_{cat}^{-1}$ $h^{-1}$.

The conversion of CO with time-on-stream for Mg—Ni, Mg—NiRu05 and Mg—NiRu10 catalysts is presented in FIG. 7. The initial CO conversion was nearly 80% in all the catalysts. The CO conversion decreases from 80% to 19% over 12 hrs for (1.5% MgO-10% Ni). Deactivation occurs at a slower rate for Mg—NiRu05 and Mg—NiRu10, which showed 45% and 70% CO conversion after 15 hrs on stream, respectively. This indicates that the stability of (Mg—Ni) is greatly enhanced by the presence of Ru content in the catalyst.

Figure 8:
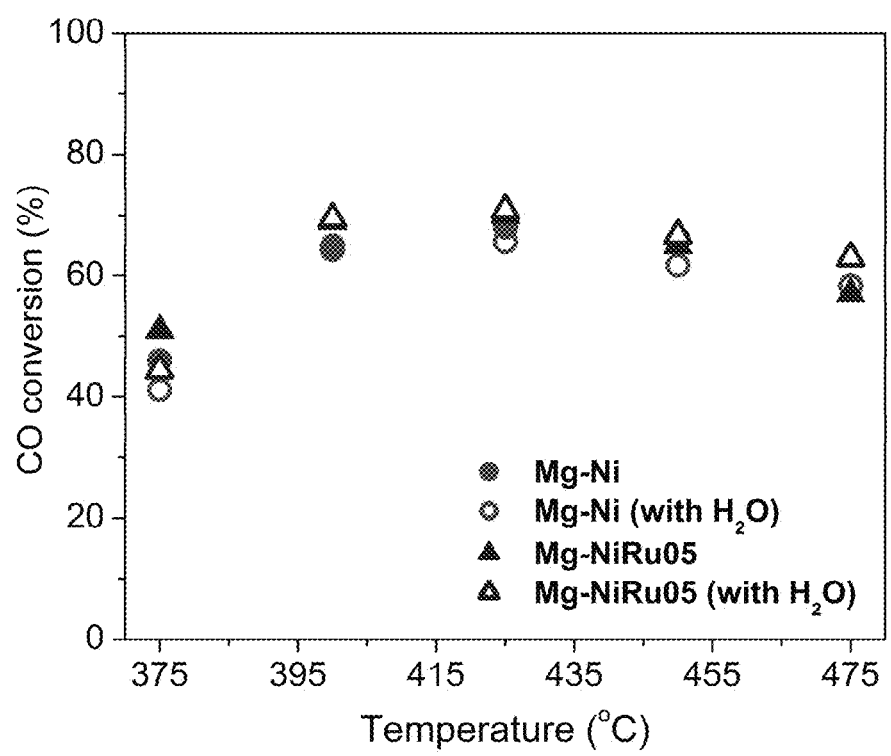
FIG. 8. Effect of $H_2O$ in Methanation activity of producer gas mixture over Mg—Ni and Mg—NiRu05 catalysts; GHSV—96000 cc $g_{cat}^{-1}$ $h^{-1}$.

The catalysts were also tested with producer gas containing 8.5% $H_2O$ in the feed mixture. The methanation activity over Mg—Ni and Mg—NiRu05 catalysts with and without $H_2O$ in the feed gas is presented in FIG. 8. It indicates that methanation activity remains similar with addition of $H_2O$. As $H_2O$ is produced in the methanation reaction, addition of extra $H_2O$ does not affect the methanation process.

Methanation with $CO+H_2+N_2$ Mixture.

Figure 9:
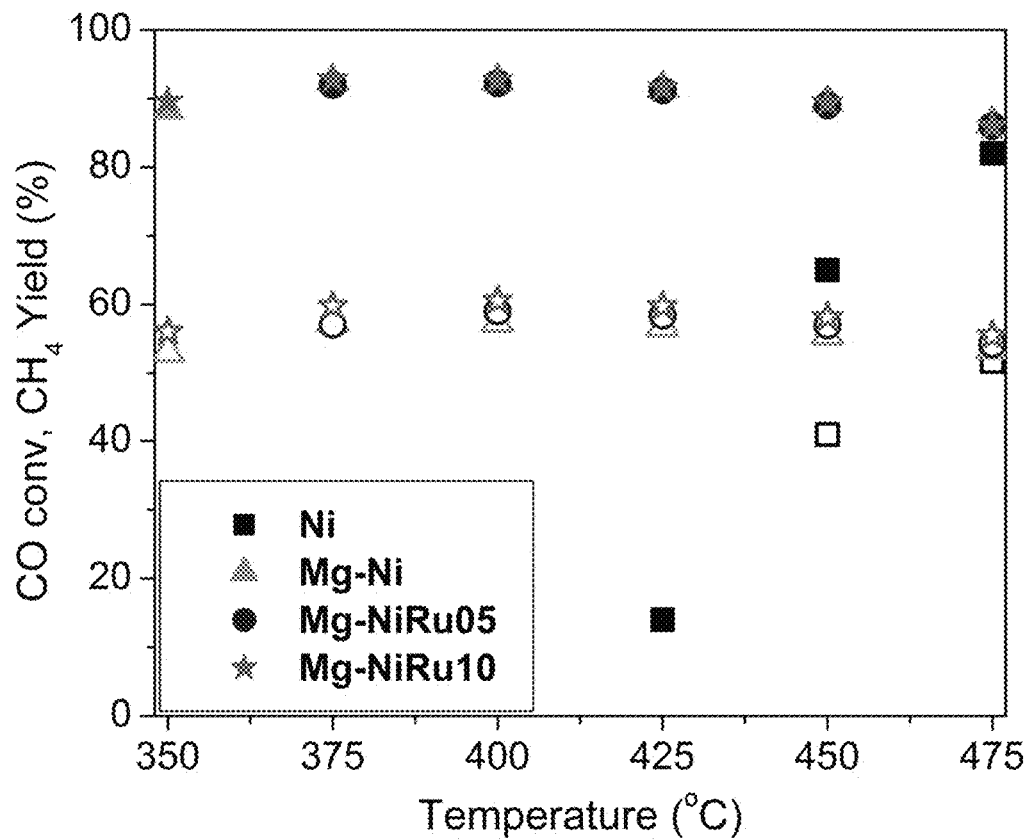
FIG. 9. A comparison of methanation activity in CO+$H_2$+$N_2$ mixture over Ni, Mg—Ni and Mg—NiRu catalysts; GHSV—96000 cc $g_{cat}^{-1}$ $h^{-1}$ (Filled symbol—CO conversion, Empty symbol—$CH_4$ Yield).

As producer gas contains both CO and $CO_2$, methanation reaction was carried out with a simple $CO+H_2$ mixture. A comparison of the CO conversion and $CH_4$ yield over Ni, Mg—Ni, and NiMgRu05 catalysts is presented in FIG. 9. A significant improvement in CO conversion due to the addition of MgO into Ni catalysts is observed. Pure Ni catalyst was active at temperatures above 450° C. reaching 80% conversion around 475° C., but MgO-promoted Ni enhances the activity significantly at lower temperatures. A CO conversion of 93% and nearly 58% $CH_4$ yield was achieved over Mg—Ni catalyst at 375° C. Further, addition of Ru into Mg—Ni did not change CO conversion, but $CH_4$ Yield was improved slightly.

Figure 10:
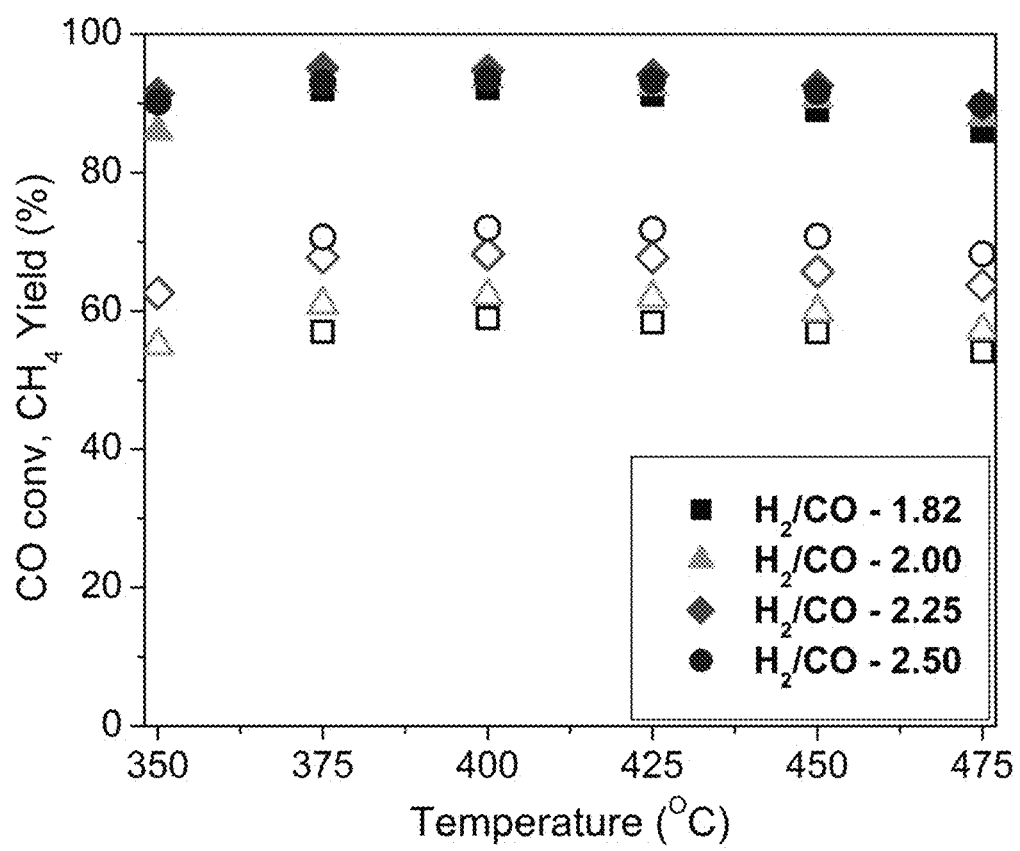
FIG. 10. Methanation activity in CO+$H_2$+$N_2$ mixture varying $H_2$/CO ratios over Mg—NiRu05 catalyst; GHSV—96000 cc $g_{cat}^{-1}$ $h^{-1}$ (Filled symbol—conversion, Empty symbol—Yield).

The conversion and selectivity of CO into $CH_4$ with variation of $H_2$/CO ratios over the Mg—NiRu05 catalyst with $H_2$/CO ratios varying from 1.82 to 2.5 is presented in FIG. 10. The $H_2$/CO ratio was increased from 1.82 by adding additional hydrogen to the stream. While CO conversion remained nearly 94% for all compositions, $CH_4$ Yield was increased from 57% to 71% as the $H_2$/CO ratio increased from 1.82 to 2.5.

Figure 11:
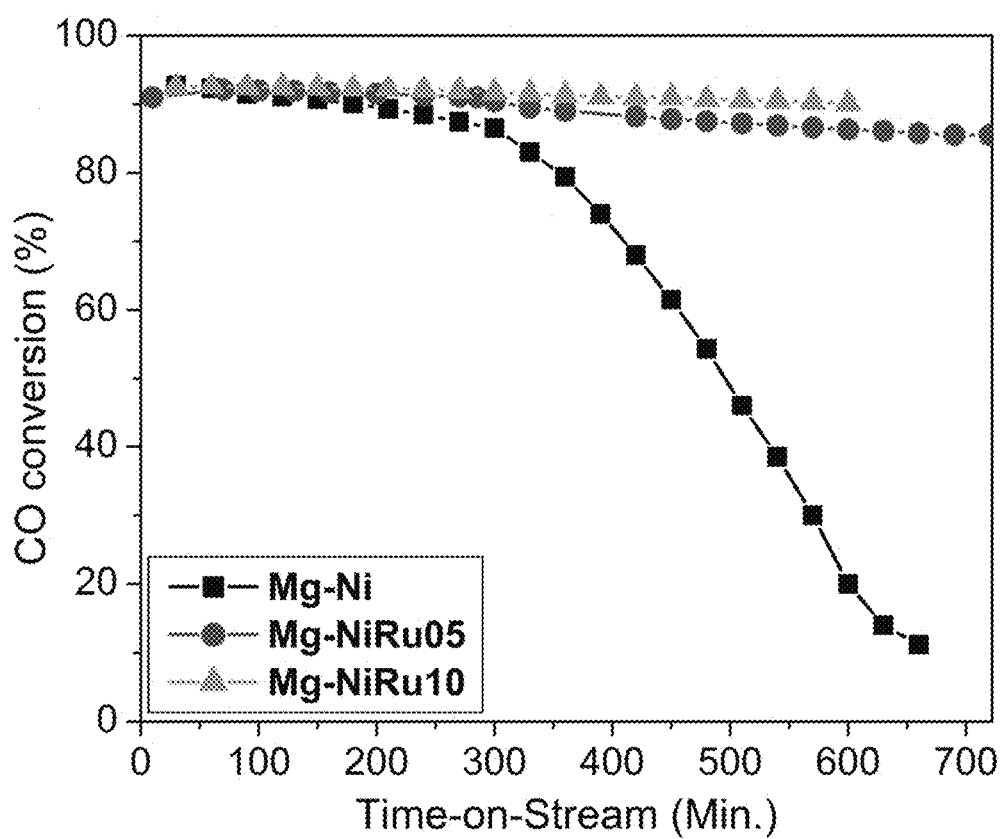
FIG. 11. Time-on-Stream for Methanation activity in CO+$H_2$+$N_2$ mixture over Mg—Ni and Mg—NiRu catalysts at 425° C.; GHSV—96000 cc $g_{cat}^{-1}$ $h^{-1}$.

A time-on-stream study over Mg—Ni and Mg—NiRu catalysts for testing stability is presented in FIG. 11. The Ru addition into Mg—Ni catalyst has a significant effect on avoiding deactivation. The deactivation of the Mg—Ni catalyst was significant, decreasing CO conversion from 90% to below 15% after 11 hrs. The activity for CO conversion was maintained and stable with Ru addition and improved with increasing Ru content. The CO conversions were found to be 86% and 90% over Mg—NiRu05 and Mg—NiRu10 catalysts, respectively, after 11 hours on stream.

Example 3. Catalyst Characterization

The catalyst characterizations were performed on Ni—Ru—MgO catalysts impregnated on an AD90 alumina ($Al_2O_3$) support. This support is composed of 40-200 micron size particles. The BET surface area of the parent $Al_2O_3$ support was 0.62 $m^2$ $g^{-1}$ and was nano-porous in nature. The measured BET surface areas for Ni, Mg—Ni, Mg—NiRu05, and Mg—NiRu10 catalysts on the support were 1.2, 3.7, 4.0, and 4.5 $m^2$ $g^{-1}$, respectively (Table 1). The increase in BET surface area in the Ni—Ru—Mg loaded samples can be contributed to nano-sized Ni or Ni—Ru particles along with highly dispersed MgO.

Figure 12:
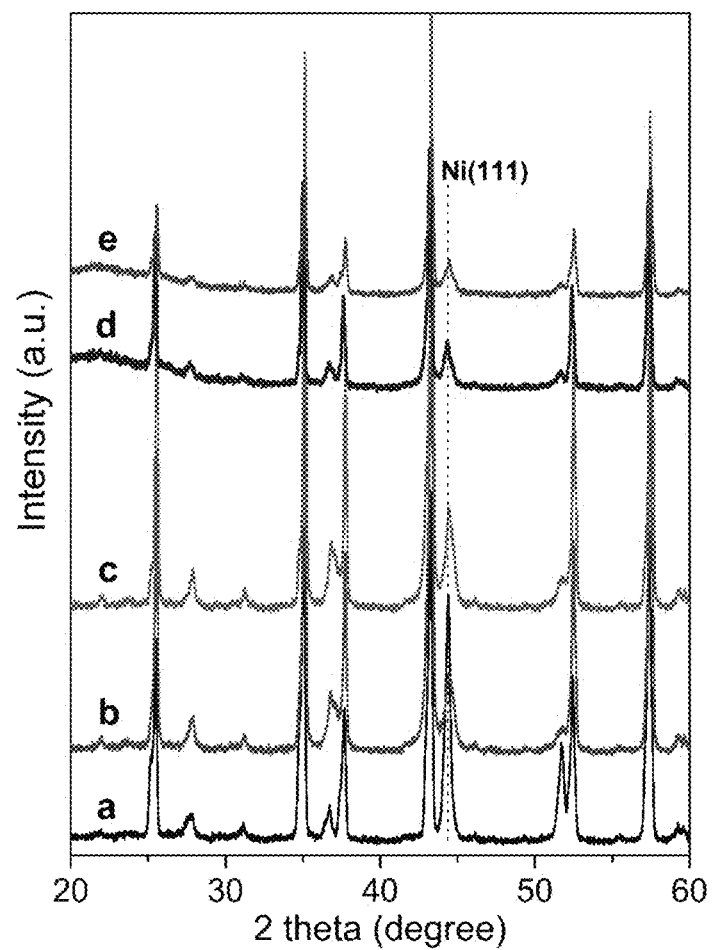
FIG. 12. XRD profiles of (line a) Ni, (line b) Mg—Ni, (line c) Mg—NiRu05, (line d) Mg—NiRu05 (used) and (line e) Mg—NiRu10 (used).

The Ni—Ru phases were characterized by XRD. The XRD profiles of Ni, Mg—Ni, Mg—NiRu05, Mg—NiRu05 (used), and Mg—NiRu10 (used) catalysts are presented in FIG. 12. The catalyst XRD profile showed the crystalline phase of $\gamma$-$Al_2O_3$. The main diffraction peak related to Ni(111) surface was observed at 44.4°. MgO could not be detected by XRD as it could be highly dispersed at the low loading of 1.5%. The position of the Ni peak remained unchanged with addition of Ru by 0.5 and 1.0%, both in freshly reduced as well as in used catalysts. No trace of MgO was found, as it easily forms hydroxide in moisture.

The morphology and elemental analysis of the catalyst surface were done by SEM technique. In FIG. 20, images of fresh (FIGS. 20A and 20B) and used (FIGS. 20C and 20D) Mg—NiRu05 catalysts are presented with 100 and 10000 times magnifications. The low-magnification images indicate nearly spherical size of the support. The highly-magnified image of the used catalyst (FIG. 20D) shows significant change in the surface as compared to the fresh (FIG. 20B) catalyst. Elemental analysis indicates significant decrease in the concentration of Ni, decreasing from 39.1% in the fresh catalyst to 23.6% in the used catalyst, as presented in FIGS. 21A and 21B. Since Ni loading is a heterogeneous phase on catalyst surface, difference in relative concentration of various elements from site to site is natural. However, if relative concentration of Ni and Ru are only considered, then it shows surface segregation of Ru in the used catalyst as compared with the fresh surface. This may be the reason of gradual decrease in the methanation activity (FIG. 7), because too much Ru reduces CO adsorption and dissociation ability of Ni. It may be possible that Ni is evaporated in absence of Ru by forming Nickel carbonyl and therefore, lower concentration of Ni in the used catalyst could be the reason for the gradual decrease in methanation activity in the Mg—NiRu05 catalyst shown in FIG. 11.

Figure 22:
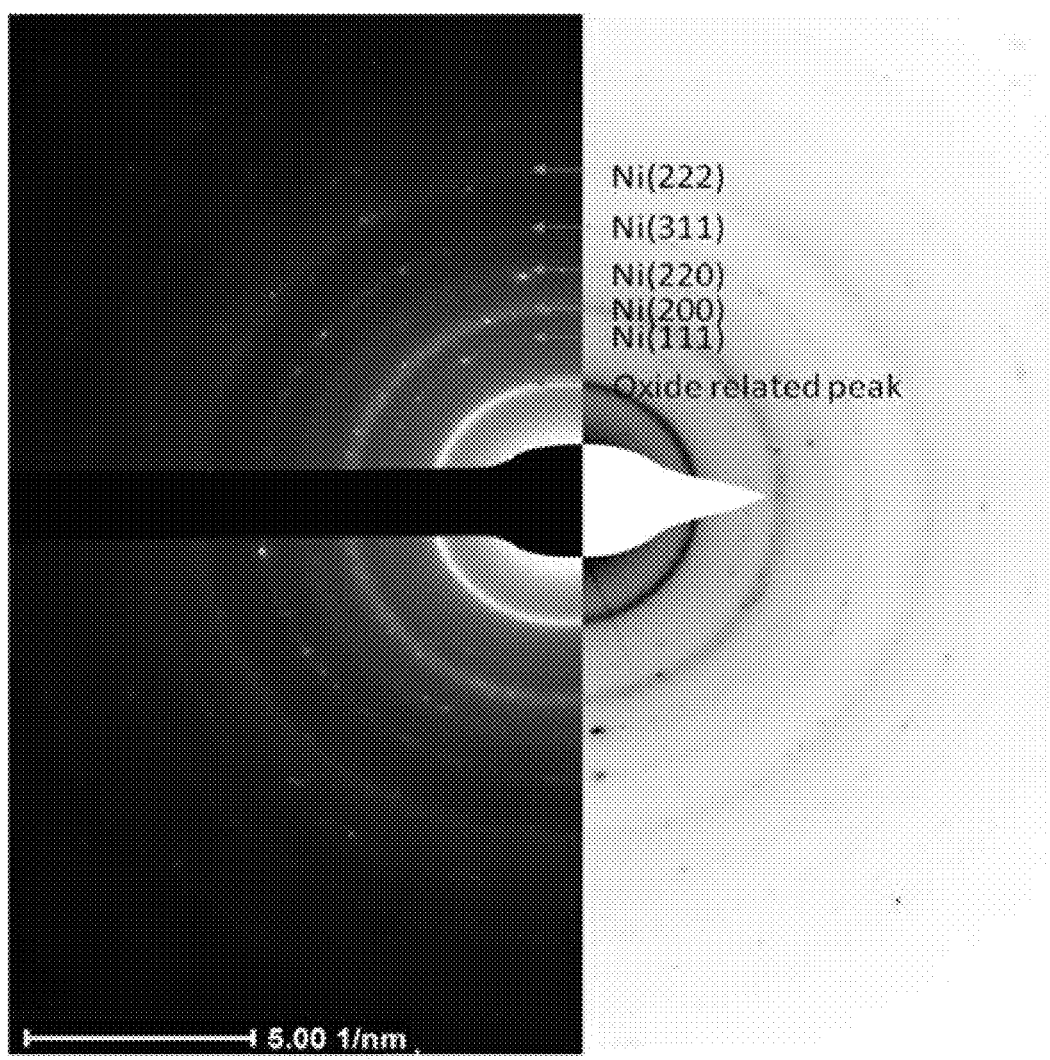
FIG. 22. Electron diffraction in fresh Mg—NiRu05 catalyst.
Figures 23A, 23B:
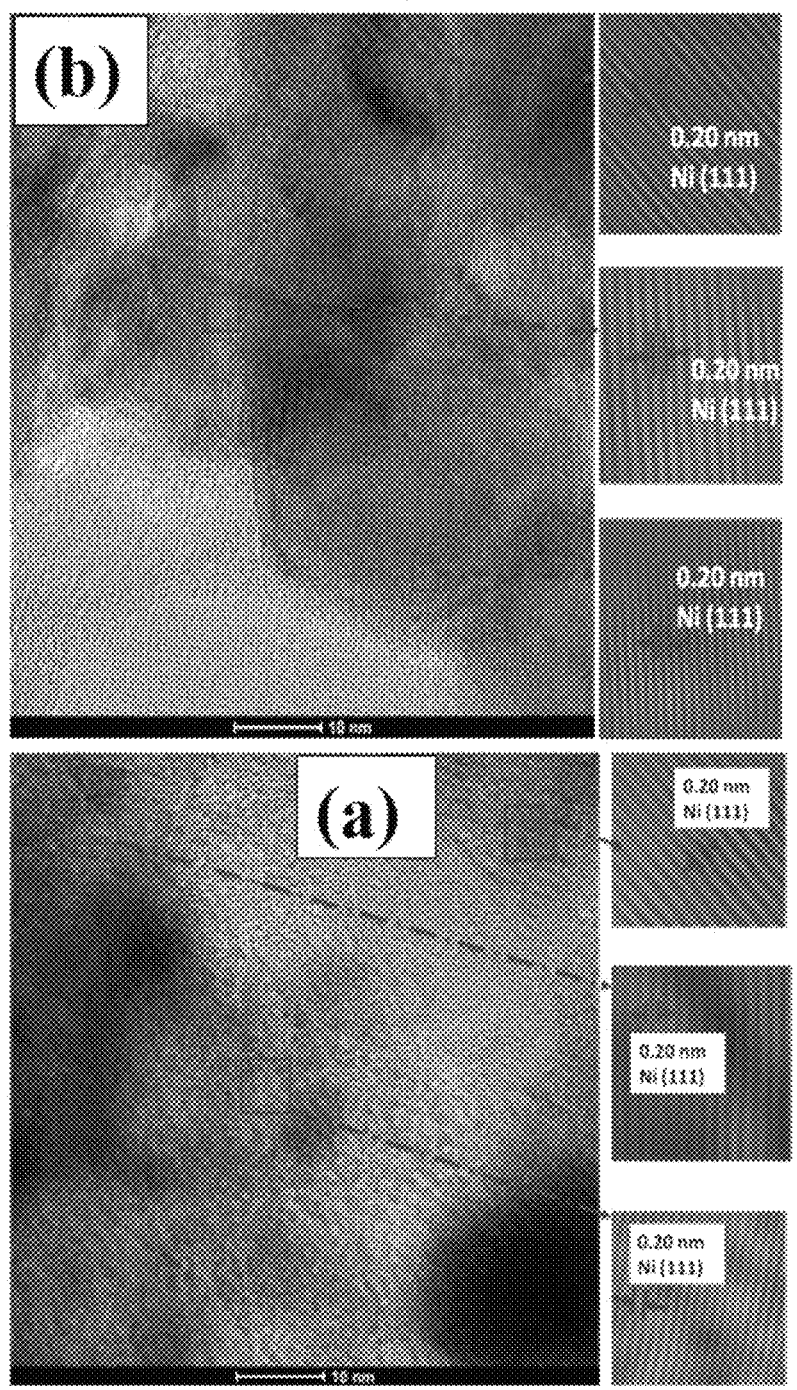
FIGS. 23A and 23B. HRTEM images in fresh Mg—NiRu05 (FIG. 23A) and used Mg—NiRu05 (FIG. 23B) catalysts.

HRTEM analysis was performed on both fresh and used Mg—NiRu05 catalyst. The electron diffraction image (FIG. 22) clearly shows the presence of Ni-metal particles in the catalysts. However, Ni (111) peak was majorly visible in the catalysts, as shown in FIGS. 16A and 16B. No Ru particle could be detected due to very low concentration but Ru was detected in the EDX analysis.

Figure 13:
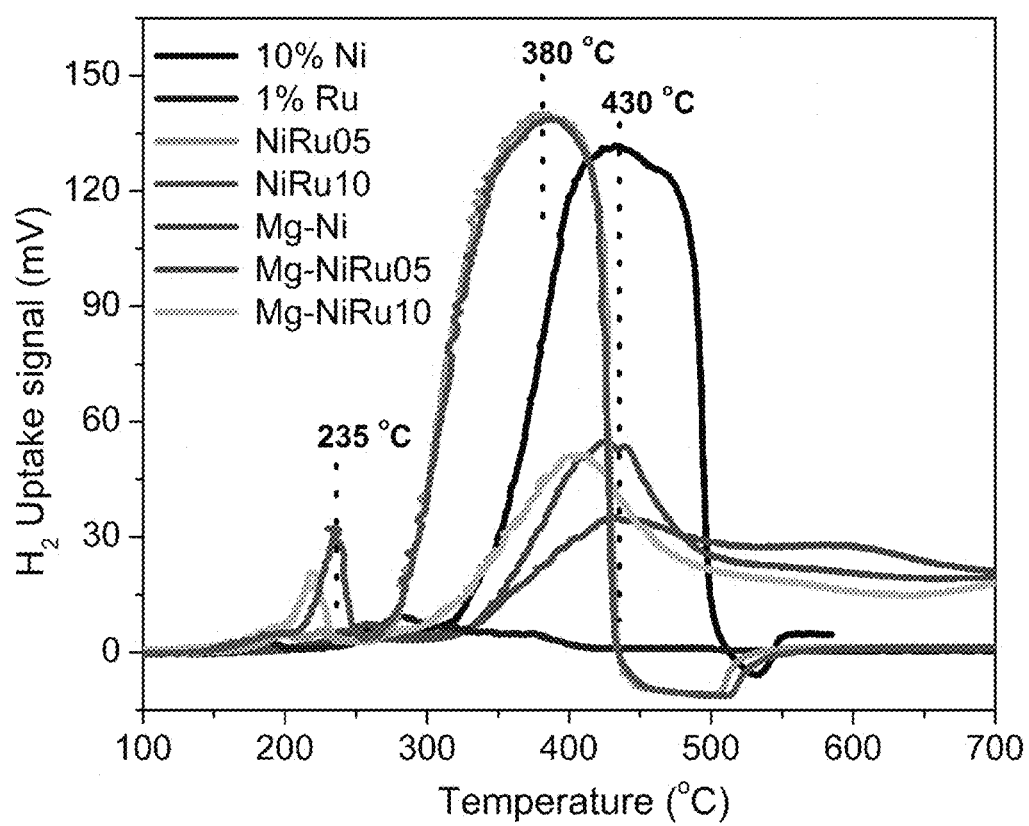
FIG. 13. $H_2$ TPR profiles of Ni, NiRu, Mg—Ni, Mg—NiRu05 and Mg—NiRu10 catalysts. (Total weight of Ni or Ni+Ru equals to 10% in the catalysts).

TPR experiments with $H_2$ were carried out to determine the reducibility of Ni in the presence of MgO, $RuO_x$, or mixtures as compared with pure Ni catalyst. TPR profiles with $H_2$ for Ni, Ru, NiRu, Mg—Ni, and Mg—NiRu catalysts are presented in FIG. 13. The reduction of pure Ni, Ru, and NiRu impregnated on $Al_2O_3$ support occurred completely at temperatures between 380° C. and 525° C. The nature of reduction of NiO on $Al_2O_3$ support was similar to literature reports, giving peak position at 430° C. With the addition of Ru into Ni, the reduction temperature was reduced from 430° C. to 380° C., indicating electronic interaction between Ru and Ni. A small reduction peak near 235° C. at a higher content of Ru indicates fine $RuO_x$ species formation. A negative signal above 500° C. was also observed in the Ni and NiRu catalysts, which could arise due to decomposition of hydride formed at lower temperatures. However, the reduction behavior of NiO was significantly changed due to the presence of MgO, and the reduction was extended to higher temperature, beyond 700° C. (FIG. 13). This was further corroborated by varying MgO loading in pure Ni loaded catalyst. This means that NiO reduction was difficult in the presence of MgO, clearly indicating the formation of solid solution, i.e $Ni_{1-x}Mg_xO_2$, and therefore, not all of the Ni content was utilized. The reduction peak at 430° C. is enhanced with addition of $RuO_x$ into Mg—Ni catalyst, and implies that $RuO_x$ cannot form a solid solution with MgO and contributed to the low temperature peak. Since catalysts were pretreated with $H_2$ at 500° C. before methanation reaction, it is important to calculate the fraction of reducible NiO from the integrated area of the TPR signal up to that temperature. The result indicates that only 31% of the NiO in Mg—Ni catalyst was reduced when compared with pure Ni-impregnated catalyst. The extent of NiO reduction in Mg—Ni was increased by the addition of Ru. Therefore, NiO reduction in Mg—NiRu05 and Mg—NiRu10 were 39% and 43.6%, respectively, assuming total reduction of Ru content in the catalysts.

Figure 14C:
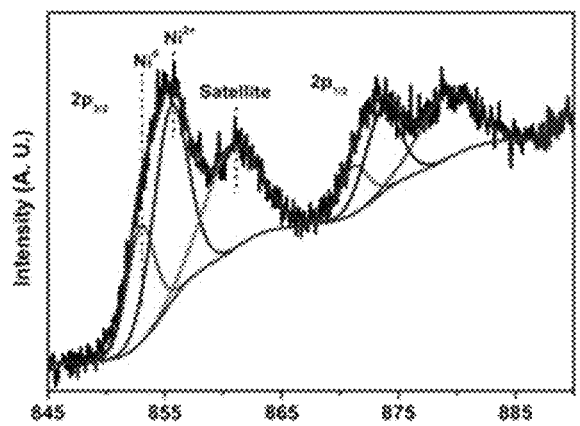
FIGS. 14A-14C. The figures show deconvoluted XP core level spectra of Ni2p in Mg—Ni, Mg—NiRu05 and Mg—NiRu10 catalysts.
Figure 14B:
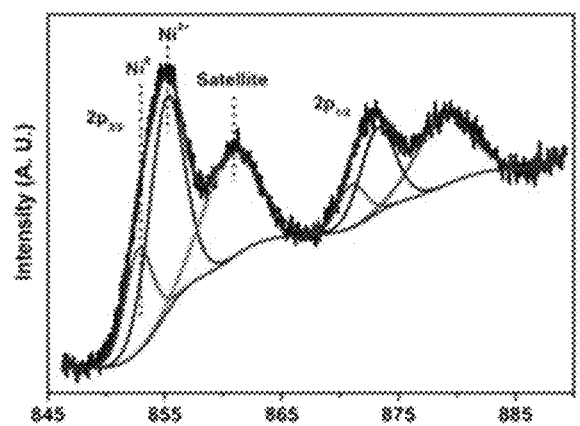
Figure 14A:
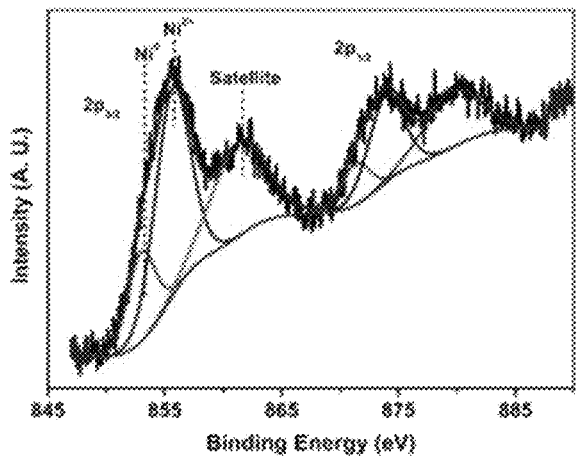
Figure 15:
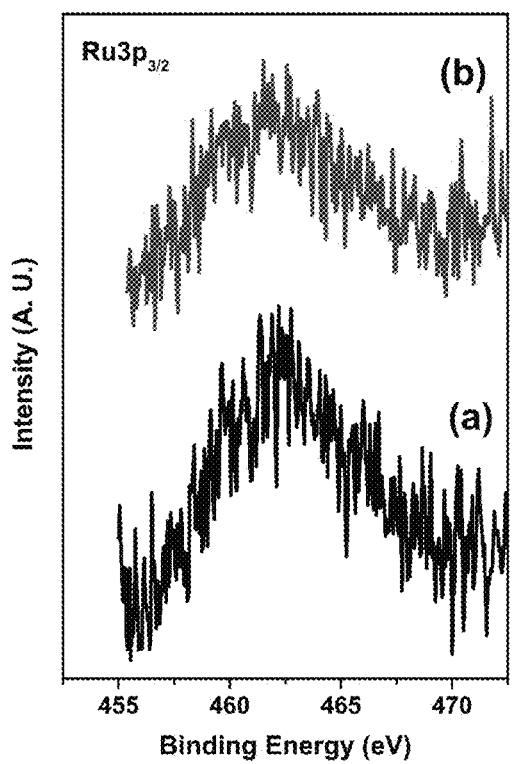
FIG. 15. XPS of Ru3p spectrum in Mg—NiRu05 and Mg—NiRu10 catalysts.

XPS measurements were performed to determine the oxidation states of Mg, Ni, and Ru in Mg—Ni, Mg—NiRu05, and Mg—NiRu10 catalysts that were pre-reduced in $H_2$ at 500° C. (similar to pre-treatment before methanation reaction). The peak in the XPS spectrum at 1303.7 eV in all catalysts correspond to $Mg^{2+}$ species. The XPS of curve-fitted Ni2p core levels in Mg—Ni, Mg—NiRu05, and Mg—NiRu10 catalysts are presented in FIG. 14A-14C. The broad character of the spectral envelopes of Ni2p indicates that Ni is present in multiple oxidation states and spectra can be curve-fitted into several component peaks. The $Ni2p_{3/2,1/2}$ peaks at 852.9 and 871.1 eV are assigned for Ni metal, and peaks at 855.5 and 873.6 eV along with characteristic satellite peaks are attributed to $Ni^{2+}$ species. Concentrations of $Ni^0$ and $Ni^{2+}$ species are calculated from the areas under the peaks. The concentration of $Ni^0$ species in Mg—Ni is 26% and increases to 28% in Mg—NiRu05. It continues to increase to 32% with increase in Ru concentration. The $H_2$ TPR also indicates nearly a 30% reduction in NiO content in the catalyst. The $Ru3p_{3/2}$ peak observed at 462.4 eV in Mg—NRu05 and Mg—NiRu10 alloys is related to $Ru^{4+}$ species and is shown in FIG. 15. Since Ru is easily oxidizable, it re-oxidizes to $Ru^{4+}$ and also promotes $Ni^0$ to $Ni^{2+}$ with increasing Ru content.

Example 4. Catalyst Performance on High-Surface-Area Supports

The development of the Mg—NiRu catalyst above was performed on the CoorsTek AD90 support with relatively low BET surface area (~0.62 m²/g). To evaluate the performance of the catalyst with respect to commercial catalysts, a higher-surface-area support is required to increase catalyst loading. Two high-surface-area alumina supports were evaluated: Delta AA400G (~80 m²/g) and Sasol PURALOX 300/200 (>100 m2/g) (see Table 2).

DELTA AA400G

To investigate the effect of catalyst loading, the Mg—NiRu05 catalyst was impregnated on the Delta AA400G alumina support (Table 2). A comparison of CO conversion activity between a commercial catalyst and the Mg—NiRu05 catalyst loaded on the higher BET surface area Delta alumina support is shown in FIGS. 16A and 16B. Since the surface of this support is very high compared to AD90 used in the development of the catalyst, the loading of 1.5% MgO+10% (Ni95Ru5) was proportionately increased up to 3% MgO+20% (Ni95Ru5). The higher 2.5% MgO+25% (Ni95Ru5) loading was less active than the 1.5% MgO+25% (Ni95Ru5) loading. The lower loading showed slightly better CO conversion below 400° C., particularly in the lower temperature range. The loading of NiRu was also increased from 10 wt % to 30 wt %, keeping MgO loading constant at 1.5 wt %. Higher CO conversion activities observed with the NiRu loading at 25% remained similar at 30%. For example, at 325° C., while 10% (Ni95Ru05) catalyst loading converted only 17% CO, this was significantly increased to nearly 95% over 30% catalyst loading, although catalytic activity reached optimum at 25% loading. A comparison of the Time-On-Stream (TOS) behavior for a commercial catalyst (Clariant METH134) and 1.5 wt % MgO+20 wt % (Ni95Ru05), 1.5 wt % MgO+25 wt % (Ni95Ru05), and 1.5 wt % MgO+25 wt % (Ni97Ru03) catalysts loaded on the Delta AA400G support are shown in FIG. 16B. The commercial catalyst was deactivated significantly, as indicated by a decrease in CO conversion from 96% to 60% after 48 hours. The Mg—NiRu05 catalysts did not display any significant deactivation up to 78 hours. Similarly, the 1.5 wt % MgO+25 wt % (Ni95Ru05) catalyst displayed only a minimal drop in CO conversion. The 1.5 wt % MgO+25 wt % (Ni97Ru3) with less ruthenium loading (97:3 weight ratio) showed slower deactivation than the

TABLE 2

Catalyst loading on high surface alumina supports, BET surface area, Bulk density and Particle size

| Catalyst | Component loading | | | BET surface area (m²/g) | Bulk density (g/cc) | Particle Size (μm) |
| --- | --- | --- | --- | --- | --- | --- |
| | MgO (g) | Ni (g) | Ru (g) | | | |
| DELTA AA400G Al₂O₃ support (10 g basis) | | | | | | |
| 1.5% MgO + 10% (Ni95Ru05) | 0.15 | 0.95 | 0.05 | 86.3 | 0.8824 | 430 |
| 1.5% MgO + 20% (Ni95Ru05) | 0.15 | 1.9 | 0.1 | 82.4 | 0.9790 | 430 |
| 3.0% MgO + 20% (Ni95Ru05) | 0.30 | 1.9 | 0.1 | — | 0.9905 | 390 |
| 1.5% MgO + 25% (Ni95Ru05) | 0.15 | 2.375 | 0.125 | 83.5 | 1.0083 | 400 |
| 2.5% MgO + 25% (Ni95Ru05) | 0.25 | 2.375 | 0.125 | — | 0.0502 | 354 |
| 1.5% MgO + 30% (Ni95Ru05) | 0.15 | 2.850 | 0.15 | — | 1.0358 | 430 |
| 1.5% MgO + 25% (Ni97Ru03) | 0.25 | 2.425 | 0.075 | — | 1.0203 | 354 |
| SASOL (PURALOX 300/200) Al₂O₃ support (10 g basis) | | | | | | |
| 1.5% MgO + 10% (Ni95Ru05) | 0.15 | 0.95 | 0.05 | — | 1.0569 | 345 |
| 1.5% MgO + 20% (Ni95Ru05) | 0.15 | 0.19 | 0.1 | — | 1.0781 | 365 |
| 2.5% MgO + 20% (Ni95Ru05) | 0.25 | 1.9 | 0.1 | — | 1.0727 | 354 |
| 1.5% MgO + 25% (Ni95Ru05) | 0.15 | 2.375 | 0.125 | 106 | — | 376 |
| 2.5% MgO + 25% (Ni95Ru05) | 0.25 | 2.375 | 0.125 | — | 1.0594 | 376 |
| 3.5% MgO + 25% (Ni95Ru05) | 0.35 | 2.375 | 0.125 | — | 1.0646 | 354 |
| 2.5% MgO + 25% (Ni97Ru03) | 0.25 | 2.425 | 0.075 | — | — | 376 | commercial catalyst. The commercial catalyst bed was found to have a blackish color, indicating coke formation may be responsible for deactivation. The stable Mg—NiRu05 catalysts did not show any indication of coke formation.

Sasol PURALOX 300/200

Figure 17:
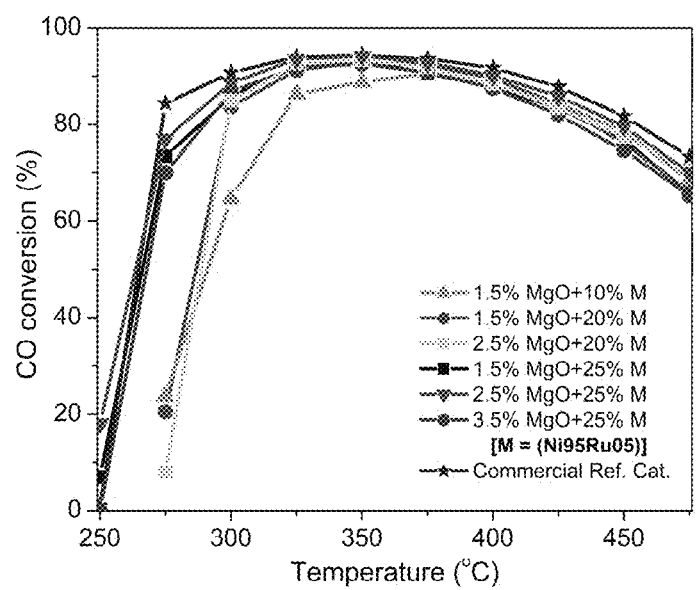
FIG. 17. A comparison of methanation activity between Commercial reference catalyst and Mg—NiRu05 catalyst over $Al_2O_3$ (SASOL PUROLOX 300/200) support with different loading of (Ni95Ru05) and MgO in the temperature range from 250 to 475° C.; GHSV=96,000 cc $min^{-1}$ $g_{cat}^{-1}$.
Figure 18:
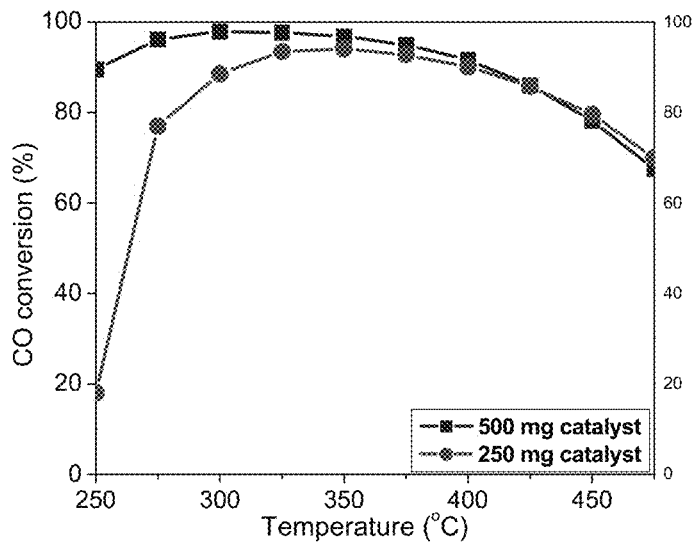
FIG. 18. CO conversion vs temperature using producer gas mixture with varying weight of 2.5% MgO+25 wt % (Ni95Ru05) catalyst loaded on $Al_2O_3$(SASOL, PUROLOX 300/200) support at 350° C.
Figure 19:
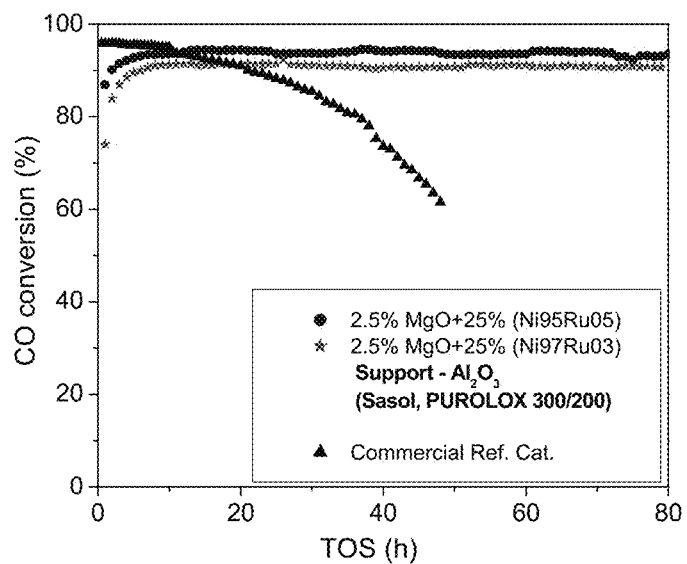
FIG. 19. Time-on-Stream for methanation activity with producer gas mixture over 2.5% MgO+25 wt % (Ni95Ru05) and 2.5% MgO+25 wt % (Ni97Ru03) catalyst loaded on $Al_2O_3$ (PUROLOX 300/200) support at 350° C.; GHSV=96,000 cc $min^{-1}$ $g_{cat}^{-1}$.

The comparison of the CO conversion activity between a commercial catalyst and the Mg—NiRu05 catalyst with varying loading of MgO as well as (Ni95Ru) on the higher-surface-area alumina support from Sasol, PURALOX 300/200, is shown in FIG. 17. The methanation activity increased significantly with increasing catalyst loading from 10% to 25%, keeping MgO content constant at 1.5% (see FIG. 18) and achieved highest activity with 25% loading. Slight increase in MgO loading from 1.5% to 2.5% with 20 or 25 wt % (Ni95Ru05) further improved CO conversion, but there was slight reduction in CO conversion with 3.5% MgO loading. Thus, a combination of 2.5% MgO and 25% (Ni95Ru05) gave the highest activity with the Sasol alumina support. The activity of 2.5 wt % MgO+25 wt % (Ni95Ru05) was very similar to the commercial catalyst over the whole temperature range. The methanation activity was increased when catalyst weight was doubled in the bed (see FIG. 18). Both, 2.5% MgO+25 wt % (Ni95Ru05) and 2.5% MgO+25 wt % (Ni97Ru03) catalysts loaded on the Sasol alumina support showed unabated methanation activity (above 90%) for at least 80 hrs as shown FIG. 19.

To conclude, a new catalyst comprising Ni, MgO, and Ru components impregnated on an $Al_2O_3$ support was prepared, and the composition was optimized based on the performance of the methanation of CO in $CO+H_2$ and producer gas mixtures. The optimum composition of 1.5 wt % MgO with 10 wt % Ni produced maximum CO conversion. Ru-to-Ni weight ratios were maintained at 95:5 and 90:10 in the catalysts. XPS studies indicated that 30% Ni exists in metal form on the surface during pretreatment with $H_2$ up to 500° C. and the remaining amount in $Ni^{2+}$ due to strong interaction with MgO in Mg—Ni catalyst. However, nearly 40% bulk reduction of Ni was found in Mg—NiRu catalysts. Both CO conversion and $CH_4$ yield were significantly improved in the Mg—Ni—Ru catalysts as compared with the Ni catalyst. The Mg—NiRu05 (1.5% MgO+9.5% Ni+0.5% Ru) and Mg—NiRu10 (1.5% MgO+9% Ni+1% Ru) catalyst compositions demonstrated significant stability during methanation of CO-containing gases as compared to that without Ru, i.e. (1.5% MgO+10% Ni). Although, Ni—Ru alloy formation was not experimentally proven, it is believed to have formed under reaction that have prevented coke-formation and deactivation of the pure Ni catalyst. Change in the morphology of the catalyst surface could be the reason for gradual decrease in catalytic activity in Mg—NiRu catalysts on low BET surface area AD 90 support. With higher BET surface area catalyst supports as demonstrated with the Delta AA400G and Sasol PURALOX 300/200, substantially increased performance at lower temperatures was observed for the Mg—NiRu catalyst. The catalyst provided comparable activity relative a commercial catalyst and demonstrated superior performance with respect to deactivation by coke formation.

It is understood that the examples described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A catalyst comprising an active catalyst component and a substrate support, the active catalyst component including nickel (Ni), magnesium oxide (MgO), and ruthenium (Ru), wherein the active catalyst component comprises about 10 to 95 wt % Ni; about 0.5 to 5.0 wt % MgO; and about 0.5 to 5 wt % Ru, and wherein the substrate support is aluminum oxide having a BET surface area of about 1.2 m²/g to about 4.5 m²/g.

2. A catalyst comprising an active catalyst component and a substrate support, the active catalyst component including nickel (Ni), magnesium oxide (MgO), and ruthenium (Ru), wherein the active catalyst component comprises about 10 to 95 wt % Ni; about 0.5 to 5.0 wt % MgO; and about 0.5 to 5 wt % Ru, and wherein the substrate support is aluminum oxide having a BET surface area of about 82.4 m²/g to about 86.3 m²/g or about 106 m²/g.

3. The catalyst of claim 2, wherein the catalyst has a particle size of about 345 μm to about 376 μm or about 354 μm to about 430 μm.

* * * * *